US012588998B1

(12) United States Patent　　(10) Patent No.: US 12,588,998 B1

Kumar et al.　　(45) Date of Patent: Mar. 31, 2026

(54) PROSTHETIC HEART VALVE FOR NATURAL BLOOD FLOW

(71) Applicant: 4C Medical Technologies, Inc., Maple Grove, MN (US)

(72) Inventors: Saravana B. Kumar, Minnetonka, MN (US); Steven D. Kruse, Maple Grove, MN (US); Jason S. Diedering, Minneapolis, MN (US)

(73) Assignee: 4C Medical Technologies, Inc., Maple Grove, MN (US)

( * ) Notice: Subject to any disclaimer, the term of this patent is extended or adjusted under 35 U.S.C. 154(b) by 0 days.

(21) Appl. No.: 19/187,060

(22) Filed: Apr. 23, 2025

Related U.S. Application Data

(63) Continuation of application No. 18/241,434, filed on Sep. 1, 2023.

(60) Provisional application No. 63/403,033, filed on Sep. 1, 2022.

(51) Int. Cl.
　　*A61F 2/24* 　　　(2006.01)
　　*G06T 7/00* 　　　(2017.01)

(52) U.S. Cl.
　　CPC ............ *A61F 2/246* (2013.01); *A61F 2/2409* (2013.01); *A61F 2/2487* (2013.01); *G06T 7/00* (2013.01); *G06T 2207/30048* (2013.01)

(58) Field of Classification Search
　　CPC .......... A61F 2/24; A61F 2/2409; A61F 2/246; A61F 2/2487; A61F 2/2412; A61F 2/2418; A61F 2/2439; A61F 2230/0071; A61F 2/2463; A61F 2240/002
　　See application file for complete search history.

(56) References Cited

U.S. PATENT DOCUMENTS

| | | | |
|---|---|---|---|
| 4,424,833 A | 1/1984 | Spector | |
| 4,503,569 A | 3/1985 | Dotter | |
| 4,733,665 A | 3/1988 | Palmaz | |
| 4,878,906 A | 11/1989 | Lindemann | |
| 5,107,838 A | 4/1992 | Yamaguchi | |

(Continued)

FOREIGN PATENT DOCUMENTS

| AU | 2014203064 B2 | 6/2015 |
|---|---|---|
| AU | 2015230879 A1 | 10/2015 |

(Continued)

OTHER PUBLICATIONS

4C Medical's Alta Valve: The First-in-Human Experience, Josep Rodes-Cabau, MD, Sep. 21, 2018.

(Continued)

*Primary Examiner* — Seema Mathew

(74) *Attorney, Agent, or Firm* — Weiss & Arons LLP

(57) ABSTRACT

A collapsible and expandable implant for implanting in a heart chamber on a side of a heart. The implant may include an outer section including a curved portion configured to be positioned in the heart chamber. The implant may be sized such that an ellipsoid conforming to the curved portion has a height greater than a length of the heart chamber by a percentage that is within a predetermined range of height percentage values. The implant may be sized such that the ellipsoid has a width greater than a width of the heart chamber by a percentage that is within a predetermined range of width percentage values. The length and width of the heart chamber may be defined in an image of the heart chamber.

126 Claims, 16 Drawing Sheets

(56)                 References Cited

U.S. PATENT DOCUMENTS

| | | | |
|---|---|---|---|
| 5,190,528 | A | 3/1993 | Fonger |
| 5,415,667 | A | 5/1995 | Frater |
| 5,441,483 | A | 8/1995 | Avitall |
| 5,693,083 | A | 12/1997 | Baker |
| 5,693,089 | A | 12/1997 | Inoue |
| 5,776,188 | A | 7/1998 | Shepherd |
| 5,843,090 | A | 12/1998 | Schuetz |
| 5,928,258 | A | 7/1999 | Khan |
| 5,957,949 | A | 9/1999 | Leonhardt |
| 5,968,070 | A | 10/1999 | Bley |
| 6,123,723 | A | 9/2000 | Konya |
| 6,152,144 | A | 11/2000 | Lesh |
| 6,231,602 | B1 | 5/2001 | Carpentier |
| 6,287,334 | B1 | 9/2001 | Moll |
| 6,319,280 | B1 | 11/2001 | Schoon |
| 6,319,281 | B1 | 11/2001 | Patel |
| 6,332,893 | B1 | 12/2001 | Mortier |
| 6,371,983 | B1 | 4/2002 | Lane |
| 6,409,758 | B2 | 6/2002 | Stobie |
| 6,425,916 | B1 | 7/2002 | Garrison |
| 6,471,718 | B1 | 10/2002 | Staehle |
| 6,494,909 | B2 | 12/2002 | Greenhalgh |
| 6,503,272 | B2 | 1/2003 | Duerig |
| 6,540,782 | B1 | 4/2003 | Snyders |
| 6,569,196 | B1 | 5/2003 | Vesely |
| 6,589,275 | B1 | 7/2003 | Ivancev |
| 6,702,826 | B2 | 3/2004 | Liddicoat |
| 6,738,655 | B1 | 5/2004 | Sen |
| 6,790,231 | B2 | 9/2004 | Liddicoat |
| 6,790,237 | B2 | 9/2004 | Stinson |
| 6,821,297 | B2 | 11/2004 | Snyders |
| 6,830,585 | B1 | 12/2004 | Artof |
| 6,840,957 | B2 | 1/2005 | Dimatteo |
| 6,875,231 | B2 | 4/2005 | Anduiza |
| 7,011,671 | B2 | 3/2006 | Welch |
| 7,041,132 | B2 | 5/2006 | Quijano |
| 7,044,966 | B2 | 5/2006 | Svanidze |
| 7,125,420 | B2 | 10/2006 | Rourke |
| 7,153,324 | B2 | 12/2006 | Case |
| 7,252,682 | B2 | 8/2007 | Seguin |
| 7,276,077 | B2 | 10/2007 | Zadno-Azizi |
| 7,276,078 | B2 | 10/2007 | Spenser |
| 7,291,168 | B2 | 11/2007 | Macoviak |
| 7,364,588 | B2 | 4/2008 | Mathis |
| 7,381,220 | B2 | 6/2008 | Macoviak |
| 7,442,204 | B2 | 10/2008 | Schwammenthal |
| 7,445,631 | B2 | 11/2008 | Salahieh |
| 7,455,689 | B2 | 11/2008 | Johnson |
| 7,510,572 | B2 | 3/2009 | Gabbay |
| 7,524,331 | B2 | 4/2009 | Birdsall |
| 7,611,534 | B2 | 11/2009 | Kapadia |
| 7,704,277 | B2 | 4/2010 | Zakay |
| 7,749,266 | B2 | 7/2010 | Forster |
| 7,758,491 | B2 | 7/2010 | Buckner |
| 7,780,723 | B2 | 8/2010 | Taylor |
| 7,789,909 | B2 | 9/2010 | Andersen |
| 7,935,144 | B2 | 5/2011 | Robin |
| 7,959,672 | B2 | 6/2011 | Salahieh |
| 7,967,853 | B2 | 6/2011 | Eidenschink |
| 7,998,196 | B2 | 8/2011 | Mathison |
| 8,012,201 | B2 | 9/2011 | Lashinski |
| 8,016,877 | B2 | 9/2011 | Seguin |
| 8,021,420 | B2 | 9/2011 | Dolan |
| 8,029,556 | B2 | 10/2011 | Rowe |
| D648,854 | S | 11/2011 | Braido |
| 8,052,592 | B2 | 11/2011 | Goldfarb |
| 8,057,493 | B2 | 11/2011 | Goldfarb |
| 8,070,802 | B2 | 12/2011 | Lamphere |
| 8,083,793 | B2 | 12/2011 | Lane |
| D653,341 | S | 1/2012 | Braido |
| D653,342 | S | 1/2012 | Braido |
| 8,092,524 | B2 | 1/2012 | Nugent |
| 8,142,492 | B2 | 3/2012 | Forster |
| 8,142,494 | B2 | 3/2012 | Rahdert et al. |
| 8,147,541 | B2 | 4/2012 | Forster |
| D660,433 | S | 5/2012 | Braido |
| D660,967 | S | 5/2012 | Braido |
| 8,167,932 | B2 | 5/2012 | Bourang |
| 8,236,049 | B2 | 8/2012 | Rowe |
| 8,246,677 | B2 | 8/2012 | Ryan |
| 8,252,051 | B2 | 8/2012 | Chau |
| 8,287,538 | B2 | 10/2012 | Brenzel et al. |
| 8,308,798 | B2 | 11/2012 | Pintor |
| 8,348,998 | B2 | 1/2013 | Pintor |
| 8,348,999 | B2 | 1/2013 | Kheradvar |
| 8,366,768 | B2 | 2/2013 | Zhang |
| 8,398,708 | B2 | 3/2013 | Meiri |
| 8,409,275 | B2 | 4/2013 | Matheny |
| 8,414,644 | B2 | 4/2013 | Quadri |
| 8,414,645 | B2 | 4/2013 | Dwork |
| 8,439,970 | B2 | 5/2013 | Jimenez |
| 8,454,686 | B2 | 6/2013 | Alkhatib |
| 8,465,541 | B2 | 6/2013 | Dwork |
| 8,491,650 | B2 | 7/2013 | Wiemeyer |
| 8,512,400 | B2 | 8/2013 | Tran |
| 8,518,106 | B2 | 8/2013 | Duffy |
| 8,535,373 | B2 | 9/2013 | Stacchino |
| 8,562,673 | B2 | 10/2013 | Yeung |
| 8,568,472 | B2 | 10/2013 | Marchand |
| 8,579,963 | B2 | 11/2013 | Tabor |
| 8,579,964 | B2 | 11/2013 | Lane |
| 8,603,159 | B2 | 12/2013 | Seguin |
| 8,623,075 | B2 | 1/2014 | Murray, III |
| 8,636,764 | B2 | 1/2014 | Miles |
| 8,641,757 | B2 | 2/2014 | Pintor |
| 8,657,870 | B2 | 2/2014 | Turovskiy |
| 8,663,318 | B2 | 3/2014 | Ho |
| 8,679,176 | B2 | 3/2014 | Matheny |
| 8,721,715 | B2 | 5/2014 | Wang |
| 8,740,976 | B2 | 6/2014 | Tran |
| 8,747,459 | B2 | 6/2014 | Nguyen |
| 8,747,461 | B2 | 6/2014 | Centola |
| 8,764,793 | B2 | 7/2014 | Lee |
| 8,764,820 | B2 | 7/2014 | Dehdashtian |
| 8,778,020 | B2 | 7/2014 | Gregg |
| 8,790,396 | B2 | 7/2014 | Bergheim |
| 8,795,354 | B2 | 8/2014 | Benichou |
| 8,795,357 | B2 | 8/2014 | Yohanan |
| 8,805,466 | B2 | 8/2014 | Salahieh |
| 8,814,931 | B2 | 8/2014 | Wang |
| 8,828,043 | B2 | 9/2014 | Chambers |
| 8,828,051 | B2 | 9/2014 | Javois |
| 8,845,711 | B2 | 9/2014 | Miles |
| 8,845,722 | B2 | 9/2014 | Gabbay |
| 8,852,271 | B2 | 10/2014 | Murray, III |
| 8,852,272 | B2 | 10/2014 | Gross |
| 8,870,949 | B2 | 10/2014 | Rowe |
| 8,876,897 | B2 | 11/2014 | Kheradvar |
| 8,906,022 | B2 | 12/2014 | Krinke et al. |
| 8,926,692 | B2 | 1/2015 | Dwork |
| 8,956,402 | B2 | 2/2015 | Cohn |
| 8,956,405 | B2 | 2/2015 | Wang |
| 8,961,518 | B2 | 2/2015 | Kyle et al. |
| 8,986,372 | B2 | 3/2015 | Murry, III |
| 8,986,374 | B2 | 3/2015 | Cao |
| 8,986,375 | B2 | 3/2015 | Garde |
| 8,998,980 | B2 | 4/2015 | Shipley |
| 8,998,982 | B2 | 4/2015 | Richter |
| 9,005,273 | B2 | 4/2015 | Salahieh |
| 9,011,527 | B2 | 4/2015 | Li |
| D730,520 | S | 5/2015 | Braido |
| D730,521 | S | 5/2015 | Braido |
| 9,023,101 | B2 | 5/2015 | Krahbichler |
| 9,050,188 | B2 | 6/2015 | Schweich, Jr. |
| 9,060,855 | B2 | 6/2015 | Tuval |
| 9,060,857 | B2 | 6/2015 | Nguyen |
| 9,060,858 | B2 | 6/2015 | Thornton |
| 9,061,119 | B2 | 6/2015 | Le |
| 9,066,800 | B2 | 6/2015 | Clague |
| 9,072,603 | B2 | 7/2015 | Tuval |
| 9,101,471 | B2 | 8/2015 | Kleinschrodt |
| 9,119,717 | B2 | 9/2015 | Wang |
| 9,132,008 | B2 | 9/2015 | Dwork |
| 9,132,009 | B2 | 9/2015 | Hacohen |

(56)                References Cited

U.S. PATENT DOCUMENTS

| | | | |
|---|---|---|---|
| 9,138,313 B2 | 9/2015 | Mcguckin, Jr. | |
| 9,144,493 B2 | 9/2015 | Carr | |
| 9,144,494 B2 | 9/2015 | Murray | |
| 9,155,619 B2 | 10/2015 | Liu | |
| 9,161,835 B2 | 10/2015 | Rankin | |
| 9,173,737 B2 | 11/2015 | Hill | |
| 9,192,466 B2 | 11/2015 | Kovalsky | |
| 9,226,820 B2 | 1/2016 | Braido | |
| 9,232,942 B2 | 1/2016 | Seguin | |
| 9,232,996 B2 | 1/2016 | Sun | |
| 9,248,016 B2 | 2/2016 | Oba | |
| 9,259,315 B2 | 2/2016 | Zhou | |
| 9,271,856 B2 | 3/2016 | Duffy | |
| 9,277,993 B2 | 3/2016 | Gamarra | |
| 9,289,289 B2 | 3/2016 | Rolando | |
| 9,289,292 B2 | 3/2016 | Anderl | |
| 9,295,547 B2 | 3/2016 | Costello | |
| 9,295,549 B2 | 3/2016 | Braido | |
| 9,301,836 B2 | 4/2016 | Buchbinder | |
| 9,301,839 B2 | 4/2016 | Stante | |
| 9,320,597 B2 | 4/2016 | Savage | |
| 9,320,599 B2 | 4/2016 | Salahieh | |
| 9,326,853 B2 | 5/2016 | Olson | |
| 9,326,854 B2 | 5/2016 | Casley | |
| 9,333,075 B2 | 5/2016 | Biadillah | |
| 9,345,572 B2 | 5/2016 | Cerf | |
| 9,351,831 B2 | 5/2016 | Braido | |
| 9,358,108 B2 | 6/2016 | Bortlein | |
| 9,364,325 B2 | 6/2016 | Alon | |
| 9,364,637 B2 | 6/2016 | Rothstein | |
| 9,370,422 B2 | 6/2016 | Wang | |
| 9,387,106 B2 | 7/2016 | Stante | |
| 9,402,720 B2 | 8/2016 | Richter | |
| 9,414,910 B2 | 8/2016 | Lim | |
| 9,414,917 B2 | 8/2016 | Young | |
| 9,427,316 B2 | 8/2016 | Schweich, Jr. | |
| 9,439,763 B2 | 9/2016 | Geist | |
| 9,439,795 B2 | 9/2016 | Wang | |
| 9,480,560 B2 | 11/2016 | Quadri | |
| 9,498,370 B2 | 11/2016 | Kyle et al. | |
| 9,504,569 B2 | 11/2016 | Malewicz | |
| 9,522,062 B2 | 12/2016 | Tuval | |
| 9,566,152 B2 | 2/2017 | Schweich, Jr. | |
| 9,579,194 B2 | 2/2017 | Elizondo | |
| 9,579,197 B2 | 2/2017 | Duffy | |
| 9,622,863 B2 | 4/2017 | Karapetian | |
| 9,717,592 B2 | 8/2017 | Thapliyal | |
| 9,730,791 B2 | 8/2017 | Ratz | |
| 9,737,400 B2 | 8/2017 | Fish | |
| 9,737,401 B2 | 8/2017 | Conklin | |
| 9,750,604 B2 | 9/2017 | Naor | |
| 9,763,780 B2 | 9/2017 | Morriss | |
| 9,795,477 B2 | 10/2017 | Tran | |
| 9,801,711 B2 | 10/2017 | Gainor | |
| 9,827,093 B2 | 11/2017 | Cartledge | |
| 9,839,517 B2 | 12/2017 | Centola | |
| 9,839,765 B2 | 12/2017 | Morris | |
| 9,861,477 B2 | 1/2018 | Backus | |
| 9,872,765 B2 | 1/2018 | Zeng | |
| 9,877,830 B2 | 1/2018 | Lim | |
| 9,968,443 B2 | 5/2018 | Bruchman | |
| 10,004,601 B2 | 6/2018 | Tuval | |
| 10,016,274 B2 | 7/2018 | Tabor | |
| 10,016,275 B2 | 7/2018 | Nyuli | |
| 10,022,132 B2 | 7/2018 | Wlodarski et al. | |
| 10,034,750 B2 | 7/2018 | Morriss | |
| 10,039,637 B2 | 8/2018 | Maimon | |
| 10,039,642 B2 | 8/2018 | Hillukka | |
| 10,098,735 B2 | 10/2018 | Lei | |
| 10,098,763 B2 | 10/2018 | Lei | |
| 10,117,742 B2 | 11/2018 | Braido | |
| 10,143,551 B2 | 12/2018 | Braido | |
| 10,182,907 B2 | 1/2019 | Lapeyre | |
| 10,195,023 B2 | 2/2019 | Wrobel | |
| 10,226,340 B2 | 3/2019 | Keren | |
| 10,231,834 B2 | 3/2019 | Keidar | |
| 10,238,490 B2 | 3/2019 | Gifford, III | |
| 10,245,145 B2 | 4/2019 | Mantanus | |
| 10,258,464 B2 | 4/2019 | Delaloye | |
| 10,299,917 B2 | 5/2019 | Morriss | |
| 10,321,990 B2 | 6/2019 | Braido | |
| 10,327,892 B2 | 6/2019 | O'Connor | |
| 10,327,893 B2 | 6/2019 | Maiorano | |
| 10,350,065 B2 | 7/2019 | Quadri | |
| 10,357,360 B2 | 7/2019 | Hariton | |
| 10,368,982 B2 | 8/2019 | Weber | |
| 10,376,363 B2 | 8/2019 | Quadri | |
| 10,383,725 B2 | 8/2019 | Chambers | |
| 10,390,943 B2 | 8/2019 | Hernandez | |
| 10,405,974 B2 | 9/2019 | Hayes | |
| 10,433,961 B2 | 10/2019 | Mclean | |
| 10,470,880 B2 | 11/2019 | Braido | |
| 10,492,907 B2 | 12/2019 | Duffy | |
| 10,500,041 B2 | 12/2019 | Valdez | |
| 10,507,107 B2 | 12/2019 | Nathe | |
| 10,512,537 B2 | 12/2019 | Corbett | |
| 10,512,538 B2 | 12/2019 | Alkhatib | |
| 10,517,726 B2 | 12/2019 | Chau | |
| 10,524,902 B2 | 1/2020 | Gründeman | |
| 10,524,910 B2 | 1/2020 | Hammer | |
| 10,531,951 B2 | 1/2020 | Spargias | |
| 10,537,427 B2 | 1/2020 | Zeng | |
| 10,555,809 B2 | 2/2020 | Hastings | |
| 10,555,812 B2 | 2/2020 | Duffy | |
| 10,561,495 B2 | 2/2020 | Chambers | |
| 10,595,992 B2 | 3/2020 | Chambers | |
| 10,610,362 B2 | 4/2020 | Quadri | |
| 10,653,523 B2 | 5/2020 | Chambers | |
| 10,667,905 B2 | 6/2020 | Ekvall | |
| 10,667,909 B2 | 6/2020 | Richter | |
| 10,702,379 B2 | 7/2020 | Garde | |
| 10,702,380 B2 | 7/2020 | Morriss | |
| 10,709,560 B2 | 7/2020 | Kofidis | |
| 10,751,169 B2 | 8/2020 | Chambers | |
| 10,751,170 B2 | 8/2020 | Richter | |
| 10,751,172 B2 | 8/2020 | Para | |
| 10,758,265 B2 | 9/2020 | Siegel | |
| 10,758,342 B2 | 9/2020 | Chau | |
| 10,779,935 B2 | 9/2020 | Scorsin | |
| 10,779,936 B2 | 9/2020 | Pollak | |
| 10,779,968 B2 | 9/2020 | Giasolli | |
| 10,786,351 B2 | 9/2020 | Christianson | |
| 10,828,152 B2 | 11/2020 | Chambers | |
| 10,856,983 B2 | 12/2020 | Keränen | |
| 10,869,756 B2 | 12/2020 | Al-Jilaihawi | |
| 10,874,513 B2 | 12/2020 | Chambers | |
| 10,945,835 B2 | 3/2021 | Morriss | |
| 10,973,630 B2 | 4/2021 | Torrianni | |
| 10,980,636 B2 | 4/2021 | Delaloye | |
| 11,000,000 B2 | 5/2021 | Diedering | |
| 11,007,053 B2 | 5/2021 | Braido | |
| 11,007,054 B2 | 5/2021 | Braido | |
| 11,013,599 B2 | 5/2021 | Subramanian | |
| 11,026,782 B2 | 6/2021 | Chambers | |
| 11,033,275 B2 | 6/2021 | Franano et al. | |
| 11,045,202 B2 | 6/2021 | Amplatz | |
| 11,065,113 B2 | 7/2021 | Backus | |
| 11,065,116 B2 | 7/2021 | Tegels | |
| 11,065,138 B2 | 7/2021 | Schreck | |
| 11,096,781 B2 | 8/2021 | Gurovich | |
| 11,147,666 B2 | 10/2021 | Braido | |
| 11,154,239 B2 | 10/2021 | Toth | |
| 11,154,396 B2 | 10/2021 | Dibie | |
| 11,154,398 B2 | 10/2021 | Straubinger | |
| 11,160,653 B2 * | 11/2021 | Benichou | A61F 2/2409 |
| 11,197,754 B2 | 12/2021 | Saffari | |
| 11,207,176 B2 | 12/2021 | Delaloye | |
| 11,278,399 B2 | 3/2022 | Liu | |
| 11,278,406 B2 | 3/2022 | Straubinger | |
| 11,318,013 B2 | 5/2022 | Mcveigh et al. | |
| 11,351,028 B2 | 6/2022 | Peterson | |
| 11,389,293 B2 | 7/2022 | Torrianni | |
| 11,395,734 B2 | 7/2022 | Lee | |
| 11,395,738 B2 * | 7/2022 | Benichou | A61F 2/2445 |

(56)  References Cited

U.S. PATENT DOCUMENTS

| | | | |
|---|---|---|---|
| 11,413,141 B2 | 8/2022 | Morin | |
| 11,419,716 B2 | 8/2022 | Braido | |
| 11,452,628 B2 * | 9/2022 | Diedering | A61F 2/9525 |
| 11,458,013 B2 | 10/2022 | Righini | |
| 11,944,537 B2 * | 4/2024 | Chambers | A61F 2/2418 |
| 11,957,577 B2 * | 4/2024 | Chambers | A61F 2/2418 |
| 11,992,403 B2 * | 5/2024 | Berndt | A61F 2/2427 |
| 12,029,647 B2 * | 7/2024 | Chambers | A61F 2/2418 |
| 12,036,113 B2 * | 7/2024 | Kumar | A61F 2/2427 |
| 12,053,375 B2 * | 8/2024 | Kumar | A61F 2/2418 |
| 12,133,797 B2 * | 11/2024 | Benson | A61F 2/2439 |
| 12,161,551 B2 | 12/2024 | Bialas et al. | |
| 12,232,991 B2 * | 2/2025 | Diedering | A61F 2/2439 |
| 12,453,630 B2 * | 10/2025 | Berndt | A61F 2/2427 |
| 2001/0005787 A1 | 6/2001 | Oz | |
| 2002/0072710 A1 | 6/2002 | Stewart | |
| 2002/0161377 A1 | 10/2002 | Rabkin | |
| 2003/0057156 A1 | 3/2003 | Peterson | |
| 2003/0083730 A1 | 5/2003 | Stinson | |
| 2003/0199971 A1 | 10/2003 | Tower | |
| 2003/0225445 A1 | 12/2003 | Derus | |
| 2003/0233141 A1 | 12/2003 | Israel | |
| 2004/0073286 A1 | 4/2004 | Armstrong | |
| 2004/0088041 A1 | 5/2004 | Stanford | |
| 2004/0138745 A1 | 7/2004 | Macoviak | |
| 2004/0210307 A1 | 10/2004 | Khairkhahan | |
| 2004/0243107 A1 | 12/2004 | Macoviak | |
| 2005/0004641 A1 | 1/2005 | Pappu | |
| 2005/0075727 A1 | 4/2005 | Wheatley | |
| 2005/0096739 A1 | 5/2005 | Cao | |
| 2005/0113861 A1 | 5/2005 | Corcoran | |
| 2005/0137622 A1 | 6/2005 | Griffin | |
| 2005/0197694 A1 | 9/2005 | Pai | |
| 2005/0273160 A1 | 12/2005 | Lashinski | |
| 2006/0142847 A1 | 6/2006 | Shaknovich | |
| 2006/0184226 A1 | 8/2006 | Austin | |
| 2006/0224183 A1 | 10/2006 | Freudenthal | |
| 2006/0229708 A1 | 10/2006 | Powell | |
| 2006/0259134 A1 | 11/2006 | Schwammenthal et al. | |
| 2006/0271173 A1 | 11/2006 | Delgado | |
| 2006/0276874 A1 | 12/2006 | Wilson | |
| 2007/0016288 A1 | 1/2007 | Gurskis | |
| 2007/0173930 A1 | 7/2007 | Sogard | |
| 2007/0233223 A1 | 10/2007 | Styrc | |
| 2007/0238979 A1 | 10/2007 | Huynh | |
| 2007/0239254 A1 | 10/2007 | Chia | |
| 2007/0239271 A1 | 10/2007 | Nguyen | |
| 2007/0270931 A1 | 11/2007 | Leanna | |
| 2007/0275027 A1 | 11/2007 | Wen et al. | |
| 2007/0293942 A1 | 12/2007 | Mirzaee | |
| 2008/0004697 A1 | 1/2008 | Lichtenstein | |
| 2008/0039928 A1 | 2/2008 | Peacock | |
| 2008/0082166 A1 | 4/2008 | Styrc | |
| 2008/0262592 A1 | 10/2008 | Jordan | |
| 2008/0269877 A1 | 10/2008 | Jenson | |
| 2008/0275540 A1 | 11/2008 | Wen | |
| 2008/0281398 A1 | 11/2008 | Koss | |
| 2008/0288042 A1 | 11/2008 | Purdy | |
| 2008/0288055 A1 | 11/2008 | Paul, Jr. | |
| 2009/0076585 A1 | 3/2009 | Hendriksen | |
| 2009/0082840 A1 | 3/2009 | Rusk | |
| 2009/0099640 A1 | 4/2009 | Weng | |
| 2009/0099647 A1 | 4/2009 | Glimsdale | |
| 2009/0125096 A1 | 5/2009 | Chu | |
| 2009/0143852 A1 | 6/2009 | Chambers | |
| 2009/0171447 A1 | 7/2009 | Von Segesser | |
| 2009/0171456 A1 | 7/2009 | Kveen | |
| 2009/0198315 A1 | 8/2009 | Boudjemline | |
| 2009/0248134 A1 | 10/2009 | Dierking | |
| 2009/0248143 A1 | 10/2009 | Laham | |
| 2009/0270967 A1 | 10/2009 | Fleming III | |
| 2009/0276039 A1 | 11/2009 | Meretei | |
| 2009/0281609 A1 | 11/2009 | Benichou | |
| 2010/0057192 A1 | 3/2010 | Celermajer | |
| 2010/0069948 A1 | 3/2010 | Veznedaroglu | |
| 2010/0168839 A1 | 7/2010 | Braido | |
| 2010/0174355 A1 | 7/2010 | Boyle | |
| 2010/0217261 A1 | 8/2010 | Watson | |
| 2010/0217262 A1 | 8/2010 | Stevenson | |
| 2010/0217382 A1 | 8/2010 | Chau | |
| 2010/0256749 A1 | 10/2010 | Tran | |
| 2010/0262157 A1 | 10/2010 | Silver | |
| 2010/0262231 A1 | 10/2010 | Tuval et al. | |
| 2011/0022151 A1 | 1/2011 | Shin | |
| 2011/0046712 A1 | 2/2011 | Melsheimer | |
| 2011/0082539 A1 | 4/2011 | Suri | |
| 2011/0082540 A1 | 4/2011 | Forster | |
| 2011/0208293 A1 | 8/2011 | Tabor | |
| 2011/0218585 A1 | 9/2011 | Krinke et al. | |
| 2011/0251676 A1 | 10/2011 | Sweeney | |
| 2011/0301702 A1 | 12/2011 | Rust | |
| 2011/0319988 A1 | 12/2011 | Schankereli | |
| 2011/0319991 A1 | 12/2011 | Hariton | |
| 2012/0016468 A1 | 1/2012 | Robin | |
| 2012/0035719 A1 | 2/2012 | Forster | |
| 2012/0078356 A1 | 3/2012 | Fish | |
| 2012/0083875 A1 | 4/2012 | Johnson | |
| 2012/0095551 A1 | 4/2012 | Navia | |
| 2012/0101567 A1 | 4/2012 | Jansen | |
| 2012/0101571 A1 | 4/2012 | Thambar | |
| 2012/0109079 A1 | 5/2012 | Asleson | |
| 2012/0197193 A1 | 8/2012 | Krolik et al. | |
| 2012/0197390 A1 | 8/2012 | Alkhatib | |
| 2012/0209375 A1 | 8/2012 | Madrid | |
| 2012/0226130 A1 | 9/2012 | De Graff | |
| 2012/0303048 A1 | 11/2012 | Manasse | |
| 2012/0323313 A1 | 12/2012 | Seguin | |
| 2013/0023852 A1 | 1/2013 | Drasler | |
| 2013/0060329 A1 | 3/2013 | Agnew | |
| 2013/0066419 A1 | 3/2013 | Gregg | |
| 2013/0079872 A1 | 3/2013 | Gallagher | |
| 2013/0090728 A1 | 4/2013 | Solem | |
| 2013/0096671 A1 | 4/2013 | Iobbi | |
| 2013/0123911 A1 | 5/2013 | Chalekian | |
| 2013/0138138 A1 | 5/2013 | Clark | |
| 2013/0150956 A1 | 6/2013 | Yohanan | |
| 2013/0178783 A1 | 7/2013 | McNamara et al. | |
| 2013/0184811 A1 | 7/2013 | Rowe | |
| 2013/0190861 A1 | 7/2013 | Chau | |
| 2013/0204311 A1 | 8/2013 | Kunis | |
| 2013/0204360 A1 | 8/2013 | Gainor | |
| 2013/0226286 A1 | 8/2013 | Hargreaves | |
| 2013/0231735 A1 | 9/2013 | Deem et al. | |
| 2013/0231736 A1 | 9/2013 | Essinger | |
| 2013/0238089 A1 | 9/2013 | Lichtenstein | |
| 2013/0274855 A1 | 10/2013 | Stante | |
| 2013/0297010 A1 | 11/2013 | Bishop | |
| 2013/0297012 A1 | 11/2013 | Willard | |
| 2013/0304197 A1 | 11/2013 | Buchbinder | |
| 2013/0310917 A1 | 11/2013 | Richter | |
| 2013/0310923 A1 | 11/2013 | Kheradvar | |
| 2013/0317598 A1 | 11/2013 | Rowe | |
| 2013/0331933 A1 | 12/2013 | Alkhatib | |
| 2014/0005768 A1 | 1/2014 | Thomas | |
| 2014/0005773 A1 | 1/2014 | Wheatley | |
| 2014/0005778 A1 | 1/2014 | Buchbinder | |
| 2014/0012371 A1 | 1/2014 | Li | |
| 2014/0018841 A1 | 1/2014 | Peiffer | |
| 2014/0018906 A1 | 1/2014 | Rafiee | |
| 2014/0031928 A1 | 1/2014 | Murphy | |
| 2014/0031951 A1 | 1/2014 | Costello | |
| 2014/0039613 A1 | 2/2014 | Navia | |
| 2014/0046433 A1 | 2/2014 | Kovalsky | |
| 2014/0046436 A1 | 2/2014 | Kheradvar | |
| 2014/0052238 A1 | 2/2014 | Wang | |
| 2014/0052241 A1 | 2/2014 | Harks | |
| 2014/0067050 A1 | 3/2014 | Costello | |
| 2014/0074151 A1 | 3/2014 | Tischler | |
| 2014/0081308 A1 | 3/2014 | Wondka | |
| 2014/0081375 A1 | 3/2014 | Bardill et al. | |
| 2014/0088696 A1 | 3/2014 | Figulla | |
| 2014/0088698 A1 | 3/2014 | Roels et al. | |
| 2014/0114340 A1 | 4/2014 | Zhou | |
| 2014/0128963 A1 | 5/2014 | Quill | |

(56) References Cited

U.S. PATENT DOCUMENTS

| | | |
|---|---|---|
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0142691 A1 | 5/2014 | Pouletty |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramani |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0277573 A1 | 9/2014 | Gill et al. |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy |
| 2014/0343665 A1 | 11/2014 | Straubinger |
| 2014/0343669 A1 | 11/2014 | Lane |
| 2014/0343670 A1 | 11/2014 | Bakis |
| 2014/0358224 A1 | 12/2014 | Tegels |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088248 A1 | 3/2015 | Scorsin |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | Mcnamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Vidlund |
| 2015/0230919 A1 | 8/2015 | Chau et al. |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1 | 11/2015 | Levi |
| 2015/0327995 A1 | 11/2015 | Morin |
| 2015/0327996 A1 | 11/2015 | Fahim |
| 2015/0327999 A1 | 11/2015 | Board |
| 2015/0328000 A1 | 11/2015 | Ratz et al. |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1 | 2/2016 | Mitra |
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |
| 2016/0030173 A1 | 2/2016 | Cai |

(56)                    References Cited

U.S. PATENT DOCUMENTS

| | | |
|---|---|---|
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | Mccann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | Mckinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramani |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331529 A1 | 11/2016 | Marchand |
| 2016/0346081 A1 | 12/2016 | Zeng |
| 2016/0354203 A1 | 12/2016 | Tuval et al. |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson |
| 2017/0079790 A1 | 3/2017 | Vidlund |
| 2017/0086973 A1 | 3/2017 | Zeng |
| 2017/0095256 A1 | 4/2017 | Lindgren |
| 2017/0100240 A1* | 4/2017 | Zeng ..................... A61F 2/2418 |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0209268 A1 | 7/2017 | Cunningham et al. |
| 2017/0231761 A1 | 8/2017 | Cohen-Tzemach et al. |
| 2017/0252191 A1 | 9/2017 | Pacetti |
| 2017/0281193 A1 | 10/2017 | Asirvatham |
| 2017/0325944 A1 | 11/2017 | Erzberger et al. |
| 2017/0333102 A1 | 11/2017 | Peterson et al. |
| 2017/0348098 A1 | 12/2017 | Rowe |
| 2017/0360570 A1 | 12/2017 | Berndt et al. |
| 2018/0014830 A1 | 1/2018 | Neumann |
| 2018/0055629 A1 | 3/2018 | Oba et al. |
| 2018/0092744 A1 | 4/2018 | Von Oepen |
| 2018/0104077 A1 | 4/2018 | Cartledge et al. |
| 2018/0116843 A1 | 5/2018 | Schreck |
| 2018/0116848 A1 | 5/2018 | Mchugo |
| 2018/0133012 A1 | 5/2018 | Nathe |
| 2018/0185184 A1 | 7/2018 | Christakis |
| 2018/0193153 A1 | 7/2018 | Brenzel et al. |
| 2018/0206983 A1 | 7/2018 | Noe |
| 2018/0206988 A1* | 7/2018 | Chambers ............. A61F 2/2418 |
| 2018/0228606 A1 | 8/2018 | Alon |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0360602 A1 | 12/2018 | Kumar |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1 | 7/2019 | Kruse |
| 2019/0224028 A1 | 7/2019 | Finn |
| 2019/0247189 A1 | 8/2019 | Dale |
| 2019/0247190 A1 | 8/2019 | Nathe |
| 2019/0321530 A1 | 10/2019 | Cambronne |
| 2019/0321531 A1 | 10/2019 | Cambronne |
| 2019/0365534 A1 | 12/2019 | Kramer |
| 2019/0365538 A1 | 12/2019 | Chambers |
| 2020/0000592 A1 | 1/2020 | Lee |
| 2020/0030088 A1 | 1/2020 | Mdlund |
| 2020/0030507 A1 | 1/2020 | Higgins |
| 2020/0069423 A1 | 3/2020 | Peterson |
| 2020/0069449 A1 | 3/2020 | Diedering |
| 2020/0100897 A1 | 4/2020 | Mclean |
| 2020/0113682 A1 | 4/2020 | Chang |
| 2020/0113719 A1 | 4/2020 | Desrosiers et al. |
| 2020/0129294 A1 | 4/2020 | Hariton |
| 2020/0155306 A1 | 5/2020 | Bonyuet |
| 2020/0163765 A1 | 5/2020 | Christianson |
| 2020/0179111 A1 | 6/2020 | Mdlund |
| 2020/0179115 A1 | 6/2020 | Chambers |
| 2020/0188101 A1 | 6/2020 | Chambers |

(56) References Cited

U.S. PATENT DOCUMENTS

| | | | |
|---|---|---|---|
| 2020/0222179 A1 | 7/2020 | Chambers | |
| 2020/0253733 A1 | 8/2020 | Subramanian | |
| 2020/0261219 A1 | 8/2020 | Kumar | |
| 2020/0276013 A1 | 9/2020 | Chambers | |
| 2020/0315678 A1 | 10/2020 | Mazzio et al. | |
| 2020/0337765 A1 | 10/2020 | Smith | |
| 2020/0368023 A1 | 11/2020 | Kheradvar | |
| 2020/0375733 A1 | 12/2020 | Diedering | |
| 2021/0236274 A1* | 8/2021 | Benson | A61F 2/9517 |
| 2021/0236276 A1* | 8/2021 | Diedering | A61F 2/2439 |
| 2021/0275297 A1 | 9/2021 | Berndt | |
| 2021/0275301 A1 | 9/2021 | Kumar | |
| 2021/0290383 A1 | 9/2021 | Chambers | |
| 2022/0031451 A1 | 2/2022 | Spence | |
| 2022/0273433 A1 | 9/2022 | Kuck et al. | |
| 2022/0338979 A1* | 10/2022 | Benichou | A61F 2/2409 |
| 2023/0218397 A1 | 7/2023 | Chambers et al. | |
| 2023/0372089 A1 | 11/2023 | Kumar | |
| 2024/0058124 A1 | 2/2024 | Montgomery et al. | |
| 2024/0138976 A1 | 5/2024 | Berndt et al. | |
| 2024/0341952 A1 | 10/2024 | Kruse et al. | |
| 2024/0366366 A1 | 11/2024 | Diedering et al. | |
| 2024/0415636 A1* | 12/2024 | He | A61F 2/2409 |
| 2025/0049564 A1 | 2/2025 | Berndt et al. | |
| 2025/0057652 A1 | 2/2025 | Kumar et al. | |
| 2025/0248805 A1 | 8/2025 | Diedering et al. | |
| 2025/0248806 A1 | 8/2025 | Diedering et al. | |
| 2025/0248812 A1 | 8/2025 | Diedering et al. | |
| 2025/0255740 A1 | 8/2025 | Diedering et al. | |
| 2025/0288414 A1 | 9/2025 | Diedering et al. | |
| 2026/0007513 A1 | 1/2026 | Ayer et al. | |

FOREIGN PATENT DOCUMENTS

| | | | | |
|---|---|---|---|---|
| AU | 2013201970 B2 | 3/2016 | | |
| CN | 2820130 Y | 9/2006 | | |
| CN | 100413471 C | 8/2008 | | |
| CN | 100444811 C | 12/2008 | | |
| CN | 101953723 A | 1/2011 | | |
| CN | 101953724 A | 1/2011 | | |
| CN | 101953725 A | 1/2011 | | |
| CN | 101953728 A | 1/2011 | | |
| CN | 101953729 A | 1/2011 | | |
| CN | 101961269 A | 2/2011 | | |
| CN | 101961273 A | 2/2011 | | |
| CN | 102036622 A | 4/2011 | | |
| CN | 201870772 U | 6/2011 | | |
| CN | 203290964 U | 11/2013 | | |
| CN | 103431931 A | 12/2013 | | |
| CN | 203379235 U | 1/2014 | | |
| CN | 103598939 A | 2/2014 | | |
| CN | 103610520 A | 3/2014 | | |
| CN | 203619728 U | 6/2014 | | |
| CN | 203677318 U | 7/2014 | | |
| CN | 104287804 A | 1/2015 | | |
| CN | 104352261 A | 2/2015 | | |
| CN | 204133530 U | 2/2015 | | |
| CN | 204181679 U | 3/2015 | | |
| CN | 204246182 U | 4/2015 | | |
| CN | 204318826 U | 5/2015 | | |
| CN | 104688292 A | 6/2015 | | |
| CN | 102985033 B | 8/2015 | | |
| CN | 204581598 U | 8/2015 | | |
| CN | 204581599 U | 8/2015 | | |
| CN | 204683686 U | 10/2015 | | |
| CN | 105596052 A | 5/2016 | | |
| CN | 105615936 A | 6/2016 | | |
| CN | 205286438 U | 6/2016 | | |
| CN | 108348270 A | 7/2018 | | |
| CN | 109789293 | 5/2019 | | |
| CN | 107252363 B | 4/2020 | | |
| CN | 111432718 A * | 7/2020 | | A61B 34/10 |
| CN | 106913909 B | 9/2020 | | |
| CN | 107007887 B | 10/2020 | | |
| DE | 102010021345 A1 | 11/2011 | | |
| EA | 033745 B1 | 11/2019 | | |
| EP | 2596754 A1 | 5/2013 | | |
| EP | 2967858 A2 | 1/2016 | | |
| EP | 2982336 A1 | 2/2016 | | |
| EP | 2967845 B1 | 8/2018 | | |
| EP | 2950752 B1 | 7/2022 | | |
| JP | 2016531722 A | 10/2016 | | |
| WO | WO1995016476 A1 | 6/1995 | | |
| WO | 1996/030060 | 10/1996 | | |
| WO | WO2009127973 A2 | 10/2009 | | |
| WO | WO2014210299 A1 | 12/2014 | | |
| WO | WO2015004173 A1 | 1/2015 | | |
| WO | WO2016100806 A1 | 6/2016 | | |
| WO | WO2019006387 | 1/2019 | | |
| WO | WO-2021064624 A1 * | 4/2021 | | A61F 2/2409 |

OTHER PUBLICATIONS

Reed Miller, Start-Up Spotlight: 4C Addresses Mitral Regurgitation with Unique 'Dome' Device, https://medtech.citeline.com/MT105076/StartUp-Spotlight-4C-Addresses-Mitral-Regurgitation-With-Unique-Dome-Device Published by Citeline on Jun. 29, 2017.

A Novel Transcatheter Mitral Valve Replacement System, Dr. Phillippe Genereux, MD, Jun. 14, 2017.

The Alta Valve™ Attributes, Challenges, and Future Programs, Dr. Philippe Genereux, MD, Jun. 22, 2018.

Ferreira-Neto et al., "Transcatheter Mitral Valve Replacement With a New Supra-Annular Valve-First-in-Human Experience with the AltaValve System," https://doi.org/10.1016/jjcin.2018.10.056, By The American College of Cardiology Foundation Published by Elsevier, Jan. 28, 2019.

Goel et al., "Transcatheter Mitral Valve Therapy with Novel Supra-Annular Alta Valve," https://doi.org/10.1016/j.jaccas.2019.10.034, Published by Elsevier on behalf of The American College of Cardiology Foundation, Dec. 18, 2019.

Hatamifar et al., "MRI Evaluation of an Atrial-Anchored Transcatheter Mitral Valve Replacement Implant," https://www.aironline.org/doj/10.2214/AJR.19.22206 American Roentgen Ray Society, Jan. 15, 2020.

Alperi et al., "Device profile of the AltaValve System for Transcatheter Mitral Valve Replacement: Overview of its safety and Efficacy," https://doi.org/10.1080/17434440.2020.1781616, Informa UK Limited, Jun. 25, 2020.

Kumar et al., "AltaValve™-A Transcatheter Mitral Valve Regurgitation Treatment Technology," Transcatheter Mitral Valve Therapy, First Edition, John Wiley & Sons Ltd., Mar. 9, 2021.

The Alta Valve Supra-Annular TS System: Device Description and Early Clinical Results, Dr. Vlasis Ninios, Jun. 10, 2022.

Transcatheter Transseptal Treatment of Patients with Severe Mitral Regurgitation using an Atrial Fixation Mitral Valve Replacement Technology, Dr. Vlasis Ninios et al., Jun. 15, 2023.

The Alta Valve™ M. Attributes, Challenges, and Future Programs, Dr. Philippe Genereux, MD, Jun. 22, 2018.

4C Medical's Alta Valve: The First-in-Human Experience, Joep Rodes-Cabau, MD, Sep. 21, 2018.

Hatamifar et al., "MRI Evaluation of an Atrial-Anchored Transcatheter Mitral Valve Replacement Implant," https://www.ajronline.org/doi/10.2214/AJR.19.22206 American Roentgen Ray Society, Jan. 15, 2020.

US Office Action in U.S. Appl. No. 19/186,997, filed Jul. 21, 2025.

US Office Action in U.S. Appl. No. 19/187,042, filed Jul. 28, 2025.

US Office Action in U.S. Appl. No. 19/187,127, filed Jul. 23, 2025.

Transcription Report of a TVT Presentation entitled "A Novel Transcatheter Mitral Valve Replacement System", Dr. Phillippe Genereux, MD, Jun. 14, 2017.

* cited by examiner

300

307

209    303

211

201

301

215

208

205

207

203

400

209   407    403

401

215

201

208

207

203

500

501

503

600

601

603

605

601

700

603

705

605

703

1000

PROSTHETIC HEART VALVE FOR NATURAL BLOOD FLOW

CROSS-REFERENCE TO RELATED APPLICATIONS

This application is a continuation of U.S. patent application Ser. No. 18/241,434, filed on Sep. 1, 2023, which is a nonprovisional of U.S. Provisional Application No. 63/403,033, filed Sep. 1, 2022, both of which are hereby incorporated herein by reference in their entireties.

BACKGROUND

Implants configured for implanting in a heart typically include anchors that extend into heart tissue to retain the implant in a desired position. The anchors may include protrusions. The anchors may include barbs. The anchors may pierce the heart tissue.

Expandable implants that engage the heart without anchors may be difficult to retain in the desired position.

It would be desirable, therefore, to provide apparatus and methods for proper implant positioning without the use of anchors.

DESCRIPTION

Figure 1:
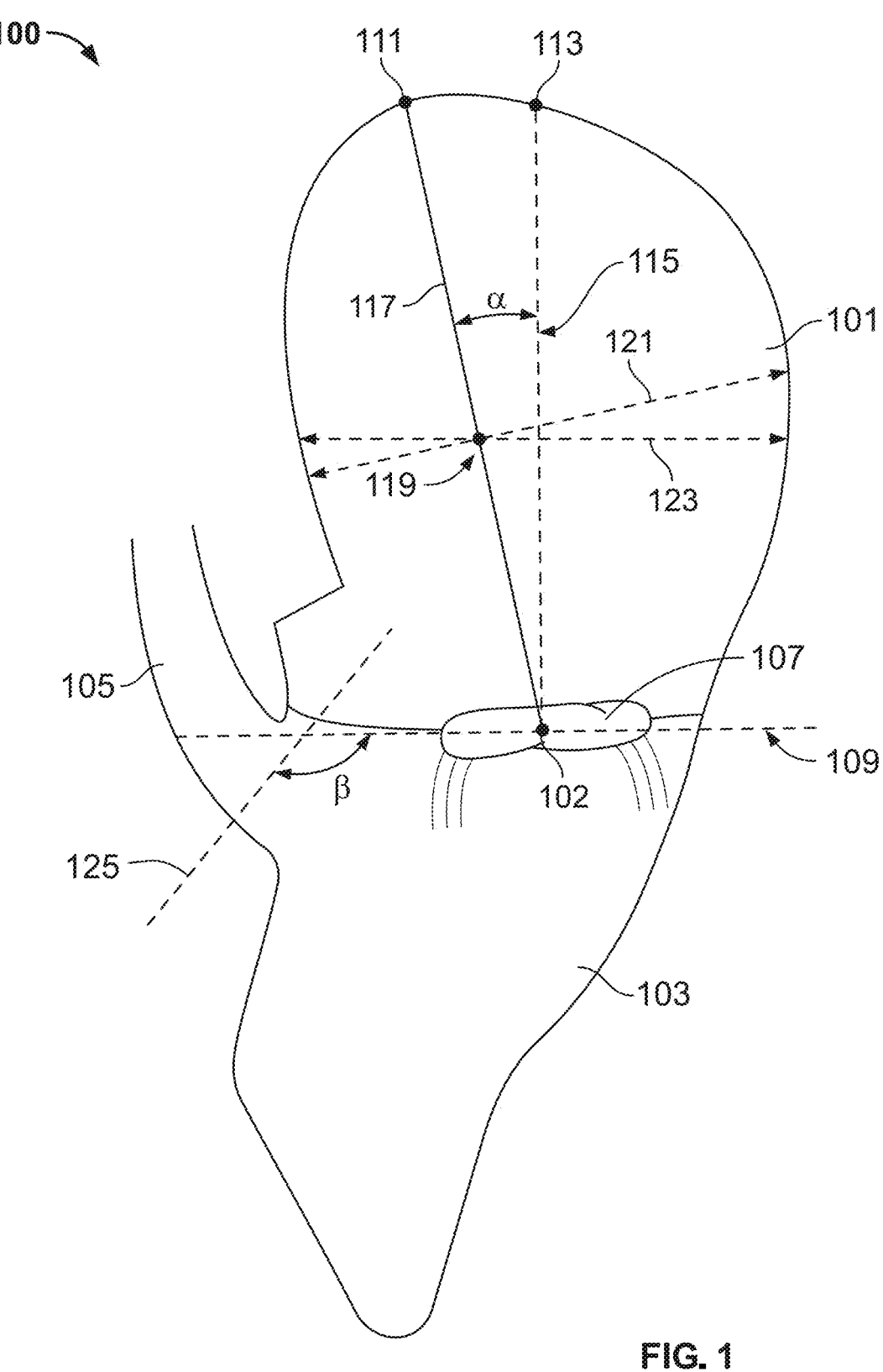
FIG. 1 shows illustrative methods in accordance with principles of the invention.

Apparatus and methods for heart valve replacement are provided. The apparatus and methods may provide a natural hemodynamic blood flow pattern. The apparatus and methods are shown and described herein with reference to the replacement of a valve in a side of a heart. The valve may be a mitral valve. The valve may be a tricuspid valve.

Apparatus and methods may include methods for ascertaining a size of an implant to be created for deployment in a heart chamber for valve replacement. The implant may be sized based at least in part on dimensions of the heart chamber. The size of the implant, when expanded, may be larger than a size of the heart chamber.

The implant may be deployed into the heart chamber by compressing the implant to fit within the heart chamber. Because the implant is sized larger than the heart chamber, the deployed implant may remain partially compressed within the heart chamber from its fully expanded size.

An outer section of the implant may engage heart tissue. The outer section may engage heart tissue without piercing the heart tissue. The outer section may be an outer section that does not include tissue piercing elements. The outer section may include a tissue-contacting surface. The entire tissue-contacting surface may be atraumatic.

The implant, therefore, may be retained in the heart chamber by pressure of the implant against the heart tissue. After deployment, the implant may elastically deflect radially in response to action of the heart. The implant may elastically deflect longitudinally in response to action of the heart. Pressure from the oversizing, of the tissue-contacting surface, against the heart tissue may prevent the annular ring from being withdrawn from the annulus by action of the heart. Pressure from the oversizing, of the tissue-contacting surface, against the heart tissue may prevent the implant from being rotated about the major and minor axes of the heart chamber by action of the heart. The oversizing may provide implant stability. Other valve replacement apparatus, in contrast, uses hooks and barbs to traumatically engage heart tissue to provide stability.

Because dimensions of a heart chamber of a first patient can vary significantly from dimensions of a heart chamber of a second patient, an implant sized to a patient's heart may provide an implant with enhanced performance. An implant oversized using systems and methods described herein may provide an implant properly sized for a given heart chamber and avoid too much oversizing, which can be damaging to heart tissue and lead to the generation of stress markers.

Additionally, oversizing using systems and methods described herein may enable the implant to move in the heart chamber during deployment to self-align a central axis of the implant with a central axis of the heart chamber. This movement may allow an inner valve support of the implant through the annulus in an orientation that provides natural hemodynamic blood flow patterns through the inner valve support into the ventricle.

The implant may include apparatus and methods described in U.S. Patent Application No. 2019/0201192, filed on Dec. 31, 2018, U.S. Patent Application No. 2021/0275297, filed on Dec. 4, 2020, and/or U.S. patent application Ser. No. 18/200,691, filed on May 23, 2023, all of which are hereby incorporated by reference herein in their entireties.

Methods of delivering and positioning the implant are described in U.S. Patent Application No. 2019/0201192, filed on Dec. 31, 2018, U.S. Patent Application No. 2021/0275297, filed on Dec. 4, 2020, and/or U.S. Patent Application No. 2020/0375733, filed on May 19, 2020, all of which are hereby incorporated by reference herein in their entireties.

Apparatus and methods may include an implant for implanting in a heart chamber on a side of a heart to replace a valve. The heart chamber may include an annulus at a bottom of the heart chamber. The annulus may define an upper annular surface. The upper annular surface may include a perimeter of the annulus. The implant may include a curved portion for being seated in the heart chamber. The implant may include an annular ring extending away from the curved portion. The annular ring may extend through the annulus and replace the valve.

The heart chamber may be a right atrium. The side of the heart may be a right side of the heart. The annulus may be a tricuspid valve annulus.

The heart chamber may be a left atrium. The side of the heart may be a left side of the heart. The annulus may be a mitral valve annulus.

The implant may be formed from superelastic materials including one or more of nickel and titanium ("Nitinol"), NiTiCu, titanium alloys, nickel alloys, spring steel alloys, carbon fiber composites, carbon-graphene, shape-memory polymers, polyisoprene-based polymers, calcium iron arsenide $CaFe_2As_2$ and similar materials. The implant may be collapsible. The implant may be self-expandable. The implant may expand in response to a force from an instrument.

The implant may include the outer section. The outer section may include the curved portion. The curved portion may be configured to be positioned in the heart chamber.

The outer section may include the annular ring extending away from the curved portion. The annular ring may be sized for being positioned in an annulus at a bottom of the heart chamber. When the heart chamber is a left atrium, the annulus may be a mitral valve. When the heart chamber is a right atrium, the annulus may be a tricuspid valve.

The implant may include an inner valve support positioned inside the outer section. The inner valve support may be configured to support leaflets. A transition section may extend between the inner valve support and the annular ring. The transition section may support the inner valve support within the outer section.

The outer section, transition section and inner valve support may include cells. The cells of each of the outer section, transition section and inner valve support may define a cell pattern. The cell patterns of the outer section, transition section and inner valve support may be the same. The cell patterns of the outer section, transition section and inner valve support may be different from each other.

The implant may be oversized relative to dimensions of the heart chamber in which the implant is to be implanted. The implant may be oversized using dimensions of a level that approximates the upper annular surface. The level may be a three-dimensional approximation of the upper annular surface. The level may be referred to alternately herein as an annular surface.

The implant may be oversized such that a three-dimensional shape conforming to some or all of an outer portion of the implant has a height greater than a length of the heart chamber. The implant may be oversized such that the three-dimensional shape conforming to some or all of the outer portion of the implant has a width greater than a width of the heart chamber. The outer portion may be a curved portion of the implant. The three-dimensional shape may have axial symmetry. The three-dimensional shape may have a longitudinal dimension and one or more radial dimensions. The three-dimensional shape may include an ellipsoid or part of an ellipsoid.

The implant may be oversized such that an ellipsoid conforming to the curved portion has a height ("ellipsoid height") that is greater than a length of the heart chamber.

The implant may be oversized such that an ellipsoid corresponding to the curved portion has an ellipsoid height that is greater than a length of the heart chamber. The ellipsoid height may be greater than the length of the heart chamber by a percentage that is within a predetermined range of height percentage values. The range may be one of several predetermined ranges.

The implant may be oversized such that the ellipsoid conforming to the curved portion has a width ("ellipsoid width") that is greater than a width of the heart chamber. The implant may be oversized such that the ellipsoid corresponding to the curved portion has an ellipsoid width that is greater than a width of the heart chamber. The ellipsoid width may be greater than the width of the heart chamber by a percentage that is within a predetermined range of width percentage values. The range may be one of several predetermined ranges.

The ellipsoid may be fitted to all of the curved portion. The ellipsoid may be fitted to part of the curved portion. The fitting may be a least squares fit.

One or both of the heart chamber length and width may be measured from an image. One or both of the heart chamber length and width may be based on a sample of measurements. One or both of the length and the width may be an average of the sample. The sample may include any suitable number of measurements, such as 2, 3, 4-5, 5-8, 9-15 or more measurements. The image may be a composite of multiple images.

A cross-section of the ellipsoid may define an ellipse. A central axis of the implant may be co-planar with the cross-section. A long axis of the ellipse may be the height of the ellipsoid. A short axis of the ellipse may be the width of the ellipsoid. When the long axis is greater than the short axis, the ellipsoid may be an ovoid. When the long axis is equal to the short axis, the ellipsoid may be a sphere.

The length and width of the heart chamber may be defined in the image of the heart chamber. The image of the heart may show a long axis view or any other suitable view. The image may be a sonogram. The image may be a computed tomography (CT) scan image. The image may be generated by taking 2D views of the left atrium from multiple orientations and using a processor to generate a 3D view of the heart chamber.

The image may be a cross-sectional view of a cross-section of the heart chamber. The image may be a cross-sectional view of the generated 3D view of the heart chamber.

The image may be a cross-sectional view taken along a long axis of the heart chamber. The long axis may be an apical long axis. The axis may extend between an anterior margin and a posterior margin of the heart chamber. When the side of the heart is a left side of the heart the cross-section may pass through a center of a mitral valve orifice and a left ventricular apex. The image may be a cross-sectional view of any other suitable cross-sectional plane through the heart chamber.

The cross-section may be cut along a cross-sectional plane. The image may define the cross-sectional plane. An intersection of the plane with the heat chamber may define a contour. An intersection of the plane with the level may define a segment.

The segment may be a straight line. The segment may be a curved line.

Points on the image that do not intersect the cross-sectional plane may be points that are not used for measuring using the systems and methods described herein.

The image may show anatomical landmarks that may be used for sizing the implant to the dimensions of the heart chamber. For example, the view may show a roof of the heart chamber, an annulus, a highest elevation point of the heart chamber, a length, and a width of the heart chamber. The view may show anatomical landmarks in one or more locations. The view may show anatomical landmarks in one or more orientations.

The image may have a scale that relates a dimension of the image to a corresponding dimension of the heart chamber. The length and the width may be measured on the image.

The image may include the level approximating the upper annular surface. The level may be overlaid on the image using numerical modeling, artificial intelligence, machine learning, or any other suitable computing technique.

The level may be computed using points selected from the upper annular surface. The points may be selected from the image. The points may be selected from the 2D views used to generate the 3D view from which the image was generated. The points may be selected from the 3D view.

The points may be selected from a commissure extending across the upper annular surface. When the side of the heart is a left side of the heart, the points may include the anterolateral commissure. The points may include the posteromedial commissure. The points may include the P2 (posterior) leaflet.

The level may be derived from a 3D spline. The level may be based on a best fit surface. The level may be based on a least squares fit of a perimeter of the spline. The level may be based on a least squares fit of an upper surface of the annulus.

The 3D spline may be generated using points selected around the periphery of the upper annular surface modeled in the 3D view of the heart chamber.

The level may be straight. The level may be curved. The level may be three-dimensional.

The length of the heart chamber may extend between the level and a point on the roof of the heart chamber in the image. The length may extend between a midpoint of the level and the point. The length may extend between a location on the level and the point. The location on the level may be anywhere within a middle third of the level or within a middle 10%, 15%, 20%, 25% or any other suitable interval of the level.

The point may be a point along a flat section of the roof in the image.

The point may be proximal to a highest point on the roof in the image. The point may be within 0-1.5 mm of the highest point. The point may be within 0-2 mm, 0.5-1.5 mm, 0-2 mm, 0.5-2 mm, or any other suitable distance from the highest point.

The point may be the highest point.

The point may be on the contour.

The highest point may be a point on the roof in the image having the greatest vertical displacement from the level. The highest point may be a point on the roof in the image having the greatest vertical displacement from a midpoint of the segment. The highest point may be a point on the roof in the image having the greatest vertical displacement from a midpoint of the level.

The highest point may be a point on the contour having the greatest vertical displacement from the level. The highest point may be a point on the contour having the greatest vertical displacement from a midpoint of the segment. The highest point may be a point on the contour having the greatest vertical displacement from a midpoint of the level. The point on the contour may be a point on the roof in the image.

When the heart chamber is a left atrium, the highest point in the image may be on an anterior side of the left atrium. The highest point in the image may be located at an acute angle relative to a vertical axis defined by a center of the annulus to a roof of the left atrium vertically above the center.

When the heart chamber is a left atrium, the roof of the heart chamber may be within 0.5-1.5 mm of a bifurcation of a pulmonary trunk and a right pulmonary artery. When the heart chamber is a right atrium, a roof of the heart chamber may be a surface parallel to an interatrial septum and spaced vertically above a tricuspid annulus at a superior atrial wall.

The length of the heart chamber may extend between the segment and the point. The length may extend between a midpoint of the segment and the point.

The length may extend between a location on the segment and the point. The location on the segment may be anywhere within a middle third of the segment or within a middle 10%, 15%, 20%, 25% or any other suitable interval of the segment.

The highest point may be located vertically above the midpoint of the level. The highest point may be located vertically above the midpoint of the segment.

The highest point on the image may be located at an acute angle relative to a vertical axis extending from the midpoint of the level to a top of the contour vertically above the midpoint. The highest point on the image may be located at an acute angle relative to a vertical axis extending from the midpoint of the segment to a top of the contour vertically above the midpoint.

The highest point on the image may be located at an acute angle relative to a vertical axis extending from the location on the level to a top of the contour vertically above the location on the level. The highest point on the image may be located at an acute angle relative to a vertical axis extending from the location on the segment to a top of the contour vertically above the location on the segment.

The point may be a first point. The width of the heart chamber may extend from a left side of the heart chamber to a right side of the heart chamber. The width may extend from a left side of the heart chamber, on the contour, to a right side of the heart chamber, on the contour. The width may intersect a second point along the length.

The second point may be intermediate between the level and the first point. The second point may be a midpoint along the length. The second point may be at a location on the length that is anywhere within a middle third of the length or within a middle 10%, 15%, 20%, or 25% of the length.

The width may be measured parallel to the level. The width may be measured parallel to the upper annular surface. The width may be measured perpendicular to the length.

The implant may include the inner valve support and the transition section extending between the annular ring and the inner valve support. Dimensions of the inner valve support may be independent of metrics derived from the image. Dimensions of the inner valve support may be preselected and not determined based on metrics derived from the image. Dimensions of the inner valve support may include a height of the inner valve support. Dimensions of the inner valve support may include a width of the inner valve support.

The heart chamber may be an atrium and the side of the heart may include a ventricle. When the implant is deployed in the atrium, the inner valve support may be configured to provide blood flow impingement on a posterior side of the ventricle during atrial contraction. The blood flow may be directed through leaflets supported by the inner valve support, through the annulus, and onto the posterior side of the ventricle.

A central axis of the inner valve support may extend along a central axis of the implant. The central axis of the implant may extend along a central axis of the atrium.

A central axis of the inner valve support may intersect the central axis of the implant at an acute angle to configure the implant to direct blood flow exiting the atrium toward a posterior side of the ventricle.

The curved portion, when expanding in the heart chamber, may move in response to pressure from walls of the heart chamber so that an implant axis converges with a central axis of the heart chamber. Movement of the curved portion may result in the implant self-aligning the implant axis with the central axis of the heart chamber. The movement may include rotation about a central axis of the implant.

The implant may move absent a force applied by an instrument. The movement of the implant may be driven by an expansion force of the curved portion against the heart chamber.

The implant axis may be a central axis of the implant. The implant axis may extend along a central axis of the curved portion.

The heart chamber may define a central axis. The central axis of the heart chamber may extend through a highest anatomical point of the heart chamber. The highest anatomical point may be a highest point on the roof of the heart chamber. The highest anatomical point may have a maximum vertical displacement from the level. The highest anatomical point may have a maximum vertical displacement from a midpoint of the level.

The highest anatomical point may be the highest point on the roof in the image. The highest anatomical point may not be on the contour.

When the heart chamber is a left atrium, the highest anatomical point may be on an anterior side of the left atrium. The highest anatomical point may be located at an acute angle relative to a vertical axis defined by the center of the annulus to a roof of the left atrium vertically above the center. The center of the annulus may be represented by a center of the level.

The central axis of the heart chamber may be oblique to a vertical axis extending from the midpoint of the level to a top of the heart chamber vertically above the midpoint.

A thickness of the annulus may define a central axis. The central axis of the heart chamber may be the central axis of the annulus. The central axis of the heart chamber may be oblique to the central axis of the annulus.

The moving may position a top of the implant at the highest anatomical point. The moving may position a hub of the implant at the highest anatomical point. The implant may not move if the implant axis is aligned with the central axis of the heart chamber.

The deployment procedure may position a top of the implant at the highest anatomical point. The deployment procedure may position a hub of the implant at the highest anatomical point.

The implant may include the annular ring. The annular ring may be sized to be anchored in the annulus. The movement of the curved portion may align an annular ring central axis with the central axis of the heart chamber. The curved portion may maintain the alignment of the annular ring central axis with the central axis of the heart chamber during a heart cycle. The heart cycle may be systole. The heart cycle may be diastole. The alignment of the annular ring central axis with the central axis of the heart chamber during systole may provide the blood flow impingement on the posterior side of the ventricle.

The implant may be oversized such that the ellipsoid height is greater than the length by a percentage within the predetermined range of height percentage values. The implant may be oversized such that the ellipsoid width is greater than the width by a percentage within the predetermined range of width percentage values.

The predetermined range of height percentage values may be 10-30. The predetermined range of height percentage values may be 10-15. The predetermined range of height percentage values may be 5-25, 5-20, 5-15, 5-10, 10-25, 10-20, 10-15, 15-30, 15-25, or 15-20.

The predetermined range of width percentage values may be 10-30. The predetermined range of width percentage values may be 10-15. The predetermined range of width percentage values may be 5-25, 5-20, 5-15, 5-10, 10-25, 10-20, 10-15, 15-30, 15-25, or 15-20.

The implant may have a wall thickness of 0.022 inches, 0.024 inches, 0.026 inches, 0.028 inches, 0.030 inches, 0.032 inches, 0.034 inches, 0.038 inches, 0.040 inches, 0.042 inches, 0.022+/−0.005 inches, 0.027+/−0.005 inches, 0.032+/−0.005 inches, 0.037+/−0.005 inches, 0.040+/−0.005 inches, 0.022+/−0.010 inches, 0.027+/−0.010 inches, 0.032+/−0.010 inches, 0.037+/−0.010 inches, 0.040+/−0.010 or any other suitable wall thickness. A predetermined range of height percentage values and a predetermined range of width percentage values described herein may be selected for an implant having a wall thickness described herein.

An increase in a wall thickness of an implant may be compensated for by a decrease in an oversizing range. An increase in a wall thickness of an implant may not change an oversizing range used.

The ellipsoid height may be selected from a range of heights. Illustrative ranges of heights may include 60 mm-90 mm, 50 mm-100 mm, 55 mm-105 mm, and any other suitable range. The ellipsoid width may be selected from a range of widths. Illustrative ranges of widths may include 60 mm-90 mm, 50 mm-100 mm, 55 mm-105 mm, and any other suitable range.

An ellipsoid height may be greater than the length by a predetermined range of height percentage values and included in a range of heights. An ellipsoid width may be greater than the width by a predetermined range of width percentage values and included in a range of widths.

The ellipsoid height may be selected from predetermined values of heights. Illustrative predetermined values of heights may start at a value of 40 mm, 45 mm, 50 mm, 60 mm, 65 mm, or any other suitable value, and increase by 1 mm, 2 mm, 3 mm, 4 mm, 5 mm, 6 mm, 8 mm, 10 mm, or any other suitable value. The ellipsoid width may be selected from predetermined values of widths. Illustrative predetermined values of widths may start at a value of 40 mm, 45 mm, 50 mm, 60 mm, 65 mm, or any other suitable value, and increase by 1 mm, 2 mm, 3 mm, 4 mm, 5 mm, 6 mm, 8 mm, 10 mm, or any other suitable value.

An ellipsoid height may be greater than the length by a predetermined range of height percentage values and selected from a predetermined value of heights. An ellipsoid width may be greater than the width by a predetermined range of width percentage values and selected from a predetermined value of widths.

In illustrative examples, when the implant is for implanting in a left atrium and is formed from Nitinol having a wall thickness of 0.022 inches, the predetermined range of height percentage values may be 10-30. The predetermined range of width percentage values may be 10-30.

In illustrative examples, when the implant is for implanting in a left atrium and is formed from Nitinol having a wall thickness of 0.022 inches, the predetermined range of height percentage values may be 10-15. The predetermined range of width percentage values may be 10-15.

In illustrative examples, when the implant is for implanting in a left atrium and is formed from Nitinol having a wall thickness of 0.022 inches, the predetermined range of height percentage values may be 5-25, 5-20, 5-15, 5-10, 10-25, 10-20, 10-15, 15-30, 15-25, or 15-20. The predetermined range of width percentage values may be 5-25, 5-20, 5-15, 5-10, 10-25, 10-20, 10-15, 15-30, 15-25, or 15-20.

In illustrative examples, when the implant is for implanting in a left atrium and is formed from Nitinol having a wall thickness of 0.022 inches, and the point is the highest point on the roof in the image, the predetermined range of height percentage values may be 5-10. The predetermined range of width percentage values may be 5-10. Thus, selecting the point as the highest point may provide a smaller oversizing range, enhancing the accuracy of the selected percentage value and decreasing uncertainty in the oversizing process. Because the implant, during expansion, moves to self-align the implant axis with the central axis of the atrium that passes through the highest anatomical point of the heart chamber, the implant will sit at the highest point on the roof in the image or very close to the highest point on the roof in the image, such as within 2 cm or less. Thus, oversizing to the highest point on the roof in the image needs a smaller oversizing range because there is less uncertainty as to where the implant will sit.

In illustrative examples, when the implant is for implanting in a left atrium and is formed from Nitinol having a wall thickness of 0.022+/−0.010 inches, the predetermined range of height percentage values may be 10-30. The predetermined range of width percentage values may be 10-30.

In illustrative examples, when the implant is for implanting in a left atrium and is formed from Nitinol having a wall thickness of 0.022+/−0.010 inches, the predetermined range of height percentage values may be 10-15. The predetermined range of width percentage values may be 10-15.

In illustrative examples, when the implant is for implanting in a left atrium and is formed from Nitinol having a wall thickness of 0.022+/−0.010 inches, the predetermined range of height percentage values may be 5-25, 5-20, 5-15, 5-10, 10-25, 10-20, 10-15, 15-30, 15-25, or 15-20. The predetermined range of width percentage values may be 5-25, 5-20, 5-15, 5-10, 10-25, 10-20, 10-15, 15-30, 15-25, or 15-20.

Example 1: Determination of Height Sizes Based on a Measured Height

| Measured height (mm) | Oversized-ellipsoid height (mm) | | Predetermined heights (mm), corresponding to different implant sizes | Predetermined heights (mm) that are within the oversized-ellipse height range (height sizes) |
| --- | --- | --- | --- | --- |
| | Low end of range 5% | High end of range 20% | | |
| 72 | 75.6 | 90.72 | 65, 70, 75, 80, 85, 90 | 80, 85, 90 |

A heart chamber height of 72 mm may be measured from the image. The oversizing range to be used may be 5-20%. The oversizing range results in an oversized-ellipsoid height range of 75.6 to 90.72 mm (72×1.05 and 72×1.20, respectively). Predetermined heights of implants may include heights of 65, 70, 75, 80, 85 and 90 mm. Of the predetermined heights, only 80, 85 and 90 mm are within the oversized-ellipsoid height range.

Example 2: Determination of Width Sizes Based on a Measured Width

| Measured width (mm) | Oversized-ellipsoid width (mm) | | Predetermined widths (mm), corresponding to different implant sizes | Predetermined widths (mm) that are within the oversized-ellipse width range (width sizes) |
| --- | --- | --- | --- | --- |
| | Low end of range 5% | High end of range 20% | | |
| 60 | 63 | 72 | 50, 55, 60 65, 70, 75 | 65, 70 |

A heart chamber width of 60 mm may be measured from the image. The oversizing range to be used may be 5-20%. The oversizing range results in an oversized-ellipsoid width range of 63 to 72 mm (60×1.05 and 60×1.20, respectively). Predetermined widths of implants may include widths of 50, 55, 60 65, 70 and 75 mm. Of the predetermined widths, only 65 and 70 mm are within the oversized-ellipsoid width range.

The selected implant may have a curved portion. An ellipsoid conforming to the curved portion may have an ellipsoid height of one of 80, 85 and 90 mm, and an ellipsoid width of one of 65 and 70 mm.

The percentage of oversizing of the implant may depend on materials used for manufacturing the implant. For example, a range of 10-30% oversizing may be used for an implant made of a flexible superelastic material such as Nitinol having a wall thickness of 0.022 inches. A smaller oversizing range may be used when the implant is made of a more rigid material. A greater oversizing range may be used when the implant is made of a less rigid material.

The implant may include the annular ring. The annular ring may have an annular ring width. The annular ring width may be greater than a width of the annulus by a percentage that is within a predetermined range of annular ring width percentage values.

The width of the annulus may be defined by the image. The width of the annulus may extend between a first commissure point in the annulus and second commissure point in the annulus. The width of the annulus may be a commissure-to-commissure distance.

The predetermined range of annular ring width percentage values may be 5-25, 5-20, 5-15, 5-10, 10-25, 10-20, 10-15, 10-30, 15-30, 15-25, or 15-20, or any other suitable range.

When the implant is for implanting in a left atrium and is formed from Nitinol having a wall thickness of 0.022 inches, the predetermined range of annular ring width percentage values may be 5-20. The predetermined range of annular ring width percentage values may be 10-20.

The annular ring width may be selected from a range of widths. An illustrative range of widths may include 35-60 mm, 40-55 mm, 38-58 mm, or any other suitable range.

The annular ring width may be selected from a discrete range of widths. An illustrative discrete range of widths may be 40, 46 and 54 mm. An illustrative discrete range of widths may include one or more of 40, 44, 48, 52 and 56. An illustrative discrete range of widths may include one or more of 40, 45, 50, 55 and 60. Any other suitable discrete range of widths may be used.

An annular ring width may be greater than the width of the annulus by a predetermined range of annular ring width percentage values and included in a range of widths. An annular ring width may be greater than the width of the annulus by a predetermined range of annular ring width percentage values and selected from a discrete range of widths.

The annular ring width may be sized to seal the annulus and prevent paravalvular leakage. Oversizing the annular ring width as described herein may seal the annulus and prevent paravalvular leakage.

An annular ring length may be sized to hit a target depth in the annulus to prevent paravalvular leakage. The target depth may be 5-20 mm. The target depth may be 5-15 mm. The annular ring length may be 10 mm, 11 mm, 12 mm, 13 mm, 14 mm, 15 mm, or between 10-11 mm, 10-12 mm, 10-13 mm, 10-14 mm, 10-15 mm, 10-16 mm, or any other suitable length.

A practitioner may thus specify an implant for a patient heart represented by the image by specifying (1) an ellipsoid height; (2) an ellipsoid width; and (3) an annular ring width.

Apparatus and methods may include determining a projected annular surface. The projected annular surface may approximate the upper annular surface. The projected annular surface may be projected from the annular surface upward from the annulus until it is tangent to the top ("roof") of the atrium. The length may be calculated as an offset from the annular surface to the projected annular surface. The projected annular surface may have a shape, such an ellipsoid. The length may be calculated as an axis of a shape that is fit to the atrium in a long axis plane. The shape may be any suitable shape.

Other methods of measuring the length may be used. The measured width may be based on the measured length.

The implant may be oversized using any suitable approach. The implant may be oversized by oversizing a volume of the implant relative to a volume of the heart chamber. The volume may be oversized by a predetermined range of percentage values such as 5-25, 5-20, 5-15, 5-10, 10-25, 10-20, 10-15, 10-30, 15-30, 15-25, or 15-20, or any other suitable range. Alternately, the volume may be oversized by a predetermined percentage, such as 5, 6, 7, 8, 9, 10, 11, 12, 13, 14, 15, 16, 17, 18, 19, 20, 21, 22, 23, 24, 25, 26, 27, 28, 29, 30, or any other suitable percentage. Thus, when the implant is deployed in the heart chamber, such as an atrium, the implant may maintain a natural volume of the atrium. The implant may be oversized by measuring a plurality of planes that pass transverse to the long axis of the image. The oversizing may be based on the measurement on the plurality of measured planes.

The implant may be shaped so as to maintain a relatively symmetrical 3D shape that best fits within the heart chamber. For example, one implant may take a spherical shape similar to a ball, and another implant may take more of an ellipsoid shape.

The oversizing of the implant has been described in connection with oversizing an ellipsoid conforming to a curved portion of the implant. Apparatus and methods include, instead of oversizing the ellipsoid height, oversizing a height of the implant. The height of the implant may be oversized such that the implant height is greater than the length by a percentage within the predetermined range of height percentage values. Apparatus and methods include, instead of oversizing the ellipsoid width, oversizing a maximum width of the implant. The maximum width may be oversized such that the maximum width is greater than the width by a percentage within the predetermined range of width percentage values.

An implant height may be greater than the length by a predetermined range of height percentage values and selected from a predetermined value of heights. An implant height may be greater than the width by a predetermined range of width percentage values and selected from a predetermined value of widths.

The height of the implant may extend between a top of the implant and a bottom of the implant. The height may extend between a hub of the implant and a bottom of the transition section. The height may extend along a longitudinal axis of the implant. The maximum width may be defined by the curved portion.

Apparatus and methods may include oversizing a first portion of an implant part to be greater than the length by a percentage within the predetermined range of height percentage values. Apparatus and methods include oversizing a second portion of the implant part to be greater than the width by a percentage within the predetermined range of width percentage values.

The first portion of the implant part may be greater than the length by a predetermined range of height percentage values and selected from a predetermined value of heights. The second portion of the implant part may be greater than the width by a predetermined range of width percentage values and selected from a predetermined value of widths.

The first portion may be a length of the implant part. The second portion may be a width of the implant part. The implant part may contact heart tissue when expanded in the heart chamber. The implant part may have any suitable shape and size.

Apparatus and methods may include methods of manufacturing the implant for implantation in the heart chamber.

The methods may include forming the curved portion of the implant. The curved portion of the implant may be formed such that the ellipsoid conforming to the curved portion has an ellipsoid height that is greater than the length by a percentage that is within the predetermined range of height percentage values. The implant may be formed such that the ellipsoid conforming to the curved portion has an ellipsoid width that is greater than the width by a percentage that is within the predetermined range of width percentage values.

The methods may include selecting the ellipsoid height from the range of heights. The methods may include selecting the ellipsoid width from the range of widths.

The methods may include selecting the ellipsoid height from the predetermined values of heights. The methods may include selecting the ellipsoid width from the predetermined values of widths.

The length may extend between the level and the point.

The point may be on the roof of the heart chamber and within 1.5 mm of the highest point on the roof in the image. The point may be within 0.5-1.5 mm of the highest point on the roof. The point may be the highest point on the roof in the image. The point may be within any other distance described herein.

The curved portion may extend along the outer section of the implant. The curved portion may be configured to be positioned in the heart chamber.

The methods may include orienting the inner valve support in the implant so the inner valve support central axis extends along the central axis of the implant. The methods may include orienting the inner valve support central axis at an acute angle relative to the implant central axis.

The methods may include using a computer program to create a first graphical model of the ellipsoid having a first cell structure. The methods may include creating a second graphical model of the annular ring having a first height and a second cell structure. The ellipsoid may have the ellipsoid height and the ellipsoid width sized as described herein. The methods may include positioning, in the computer program, the first graphical model against the second graphical model such that the ellipsoid is in contact with a top of the annular ring. The methods may further include determining that the first height is less than a threshold value. The threshold value may be 8 mm, 9 mm, 10 mm, 11 mm, 12 mm, or any other suitable value.

The methods may include increasing the first height to a second height to create a third graphical model. The methods may include positioning, in the computer program, the first graphical model against the third graphical model such that the ellipsoid is in contract with a top of the revised annular ring. The methods may include determining that the annular ring is now greater than the threshold value. The methods may include forming the annular ring such that the annular ring has the second height.

The methods may include selecting a first cell density of the implant when the ellipsoid height is less than a predetermined first value. The methods may include selecting the first cell density when the ellipsoid width is less than a predetermined second value. The methods may include selecting the first cell density when both the ellipsoid height and the ellipsoid width are less than the predetermined first value.

The methods may include selecting a second cell density of the implant when the ellipsoid height is greater than the predetermined first value. The methods may include selecting the second cell density when the ellipsoid width is greater than the predetermined second value. The methods may include selecting the second cell density when both the ellipsoid height and the ellipsoid width are greater than the predetermined first value.

The methods may include selecting the first cell density or the second cell density when the ellipsoid height is equal to the predetermined first value. The methods may include selecting the first cell density or the second cell density when the ellipsoid width is equal to the predetermined second value. When the ellipsoid height and the ellipsoid width are equal to the predetermined first value, the methods may include selecting the first cell density. When the ellipsoid height and the ellipsoid width are equal to the predetermined first value, the methods may include selecting the second cell density.

The predetermined first value may be equal to the predetermined second value. The predetermined first value may be different from the predetermined second value.

The second cell density may be greater than the first cell density. The second cell density may be less than the first cell density.

The predetermined first value may be 50 mm, 55 mm, 60 mm, 65 mm, 70 mm, 75 mm, 80 mm, 85 mm, 90 mm, or any other suitable value. The predetermined second value may be 50 mm, 55 mm, 60 mm, 65 mm, 70 mm, 75 mm, 80 mm, 85 mm, 90 mm, or any other suitable value.

The first cell density may be 5, 6, 7, 8, 9, 10, 11, 12, 13, 14, 15 or 16 cells about a maximum width of the implant.

The second cell density may be 8, 9, 10, 11, 12, 13, 14, 15 or 16, 17, 18, 19 or 20 cells about a maximum width of the implant.

In illustrative embodiments, if an ellipsoid height is less than 80 mm and an ellipsoid width is less than 80 mm, the first cell density may be selected. If an ellipsoid height is greater than 80 mm and an ellipsoid width is greater than 80 mm, the second cell density may be selected. The first cell density may be 12. The second cell density may be 15.

The methods may include selecting the first cell density of the implant when the implant height is less than the predetermined first value and/or the implant width is less then the predetermined second value. The methods may include selecting the second cell density of the implant when the implant height is greater than the predetermined first value and/or the implant width is greater than the second predetermined value.

In some embodiments, for a human heart chamber or for an animal heart chamber, the methods may include not selecting an ellipsoid height greater than a maximum ellipsoid height value and not selecting an ellipsoid width greater than a maximum ellipsoid width value. The maximum values may be different for each species into which the implant is to be implanted.

For example, maximum ellipsoid height-ellipsoid width values for a human may be 95-95 mm, 100-100 mm, 105-105 mm, 110-110 mm, 115-115 mm, 120-120 mm, 125-125 mm or any other suitable values.

The methods may include forming the inner valve support inside the implant. The forming the implant may include cutting laser tube stock to form cells and using a mandrel to shape the cut tube to form the curved portion, the annular ring, the transition section and the inner valve support. The tube stock may have a thickness of 0.022 inch, 0.022 inch+/=0.010 inch, or any other suitable thickness. The methods may include forming the transition section to span between the annular ring extending away from the curved portion and the inner valve support. The methods may include heat-treating a formed implant to set a shape that the implant will take when deployed in the heart. The implant may be monolithic. The inner valve support may be configured to provide, when the implant is deployed in the atrium, blood flow impingement on a posterior side of the ventricle during atrial contraction.

The methods may include forming the implant from a superelastic material. The methods may include forming the implant from an alloy of nickel and titanium or any other suitable elastic material described herein.

The methods may include forming an entire tissue-contacting surface of the outer section of the implant to be atraumatic. The methods may include forming the implant to be collapsible for deployment into the heart chamber and thereafter expandable such that the implant is anchorable within the atrium by pressured contact with the heart chamber and does not pierce tissue in the side of the heart.

The methods may include forming the annular ring to extend away from the curved portion. The methods may include sizing the annular ring to be positioned in the annulus. The methods may include sizing the annular ring width to be greater than the width of the annulus by a percentage that is within the predetermined range of annular ring width percentage values.

The methods may include selecting the annular ring width from the range of widths. The methods may include selecting the annular ring width from the discrete range of widths.

The methods may include sizing the annular ring width to seal the annulus and prevent paravalvular leakage. The methods may include sizing the annular ring length to hit the target depth in the annulus to prevent paravalvular leakage.

Apparatus and methods may include methods for providing an implant for implantation in a heart chamber. The methods may include identifying the level in the image. The methods may include identifying the contour in the image. The methods may include deriving from the image the length and the width.

The methods may include providing the implant such that the curved portion is sized based on the length on the width. In illustrative embodiments, an ellipsoid conforming to the curved portion of the implant may have an ellipsoid height and an ellipsoid width oversized as described herein. The methods may include providing the implant such that an annular ring height is oversized as described herein. The methods may include providing the implant such that the annular ring length is selected as described herein.

Apparatus and methods may include computer-implemented methods for sizing the implant for implanting in a heart chamber.

The methods may include generating the image. Generating the image may include creating a three-dimensional image using a plurality of two-dimensional CT scans of the heart chamber. An illustrative program that may be used to generate the three-dimensional image from two-dimensional views may be Mimics from Materialise NV.

The methods may include receiving a selection of points along an upper annular surface of an annulus displayed in the three-dimensional image. The methods may include using three-dimensional mapping or numerical modeling to generate, using the selected points, the level. The level may be a three-dimensional plane.

The methods may include using machine learning to generate the level. The methods may include feeding the image to a machine-learning algorithm and receiving from the machine-learning algorithm an output including the image and the level overlaid on the image. The machine-learning algorithm may be trained using a dataset including a plurality of images, each image including points selected to approximate an upper annular surface. The dataset may include images, each image having a level overlaid on the image.

The methods may include taking a cross-section of the three-dimensional image including the level along a long axis such as an apical long axis to obtain the image.

The methods may include identifying, using a processor, the segment and the contour. The methods may include identifying, using the processor, a midpoint of the segment.

The methods may include identifying, using the processor, the point on the roof of the heart chamber.

The methods may include measuring, using the processor, the length.

The point may be a first point. The methods may include determining, using the processor, the second point. The methods may include measuring, using the processor, the width.

The methods may include outputting implant measurements. The implant measurements may be used to manufacture the implant. The implant measurements may include the ellipsoid height. The implant measurements may include the ellipsoid width. When one or more ellipsoid heights can be selected, the methods may include outputting the one or more ellipsoid heights. When one or more ellipsoid widths can be selected, the methods may include outputting the one or more ellipsoid widths. The output may be a range. The output may be predetermined values.

Methods, including measurements and selection of sizing ranges described herein, may be performed using the processor.

In some embodiments, the methods may include using a processor to determine a width for enlargement by analyzing a selected shape, such as a 2D shape, such as an ellipse, or a 3D shape, such as an ellipsoid, that surrounds possible widths in the heart chamber. The methods may include using the processor to execute a least mean square analysis of the fit of the selected shape across the possible widths to determine which one of the possible widths would best fit the shape of the heart chamber.

The methods may include sizing an atrial implant for implantation in the atrium. The atrial implant may be the implant. The atrium may be on a side of a heart. The side of the heart may be a first side of the heart. The atrial implant may be a left atrial implant and the side of the heart may be a left side of the heart. The atrial implant may be a right atrial implant and the side of the heart may be a right side of the heart.

The methods may include identifying a center of an annulus of the side of the heart based on the image. The image of the heart may include one of a computed tomography (CT) scan image or a sonagram.

The methods may include identifying a highest elevation point of the atrium based on the image. The highest elevation point may be the highest relative to a plane corresponding to the annulus. The plane corresponding to the annulus may be referred to as an annular plane or a mitral valve plane. The plane corresponding to the annulus may be a horizontal plane. The plane corresponding to the annulus may correspond to an upper annular surface of the annulus. The plane corresponding to the annulus may be the level.

The center of the annulus may be a center of the plane. The center of the annulus may be a center of the plane in the image.

The highest elevation point may be located at an acute angle relative to a vertical axis defined by the center of the annulus to a top of the atrium vertically above the center. The highest elevation point may be highest on an anterior side of the atrium.

The methods may include measuring a length between the highest elevation point and the center. The methods may include determining a point along the length intermediate between the highest elevation point and the center. The methods may include measuring a width of the atrium from an anterior margin to a posterior margin at the point along the length.

The methods may include providing an implant having a second length that is within a range of between 5-30% greater than the length of the atrium. The second length may be a height of the implant from a top of the implant to a bottom of the implant along a central axis of the implant. The second length may be a distance between an implant hub and a bottom of the implant. The second length may be the ellipsoid height.

The methods may include providing an implant having a second width that is within a range of between 5-30% greater than the width of the atrium. The second width may be a maximum width of the curved portion of the implant. The second width may be the ellipsoid width.

The width may be measured parallel to the plane corresponding to the annulus. The width may be measured perpendicular to the length. The point at which the width is measured may be a midpoint along the length intermediate between the highest elevation point and the center of the annulus.

The methods may include selecting the second length and the second width, wherein the second length and the second width are greater by the same percentage. For example, the second length may be 15% greater than the length and the second width may be 15% greater than the width.

The atrial implant may be collapsible for deployment into the atrium of the heart and thereafter expandable such that the atrial implant is anchorable within the atrium. The atrial implant may be configured to provide blood flow impingement directed from the atrium toward a posterior side of a ventricle on the side of the heart during atrial contraction when the atrial implant is deployed in the atrium.

The atrial implant may include an annular ring sized to be anchored within the annulus.

The methods may include orienting an inner valve support by a second acute angle to configure the atrial implant to direct blood flow exiting the atrium toward a posterior of the heart when the atrial implant is deployed in the atrium.

Apparatus and methods may include methods for sizing an atrial implant for implantation into an atrium on a side of a heart. The methods may include identifying a center of an annulus of the side of the heart based on the image. The methods may include identifying a highest elevation point of the atrium based on the image. The highest elevation point may be highest relative to a plane corresponding to the annulus. The methods may include measuring a length between the highest elevation point and the center. The methods may include determining a point along the length intermediate between the highest elevation point and the center. The methods may include measuring a width of the atrium from an anterior margin to a posterior margin at the point along the length.

Apparatus and methods may include computer-implemented methods for sizing an atrial implant for implantation into an atrium on a side of a heart. The atrial implant may be a left atrial implant, the side of the heart may be a left side of the heart and the atrium may be a left atrium. The atrial implant may be a right atrial implant, the side of the heart may be a right side of the heart and the atrium may be a right atrium.

The methods may include identifying, using a processor, a center of an annulus of the side of a heart based on the image. The methods may include identifying, using the processor, a highest elevation point of the atrium based on the image. The highest elevation point may be the highest relative to a plane corresponding to the annulus. The methods may include measuring, using the processor, a length between the highest elevation point and the center. The methods may include determining, using the processor, a point along the length intermediate between the identified highest elevation point and the center. The methods may include measuring, using the processor, a width of the atrium from an anterior margin to a posterior margin at the point along the length. The methods may include providing the measurements to obtain an implant such that the implant has a second length and a second width. The second length may be 5-30% greater than the second length of the left atrium. The second width may be 5-30% greater than the second width of the left atrium.

The methods may include taking 2D views of the left atrium from multiple orientations. The sizing may include using a processor to generate a 3D view of the left atrium.

Apparatus and methods may include an atrial implant that is sized in accordance with methods described herein. The atrial implant may be collapsible for deployment into an atrium of the heart and thereafter expandable such that the atrial implant is anchorable within the atrium. The atrial implant may include a cuff that is sized to be anchored within an annulus of the side of the heart extending between the atrium and a ventricle included in the side of the heart. The cuff may be the annular ring.

The atrial implant may be configured to provide blood flow impingement, directed from the atrium, on a posterior side of a ventricle of the side of the heart during atrial contraction when the atrial implant is deployed in the atrium. For example, when the atrial implant is a left atrial implant, the implant may be configured to provide blood flow impingement, directed from the left atrium, on a posterior side of a left ventricle of the heart during atrial contraction when the implant is deployed in the left atrium.

Apparatus and methods may include an atrial implant. The atrial implant may have an expandable prosthetic frame deployable within an atrium on a side of a heart. The atrium may be a left atrium and the side of the heart may be a left side of the heart. The atrium may be a right atrium and the side of the heart may be a right side of the heart.

The atrial implant may include the annular ring coupled to the expandable prosthetic frame to be anchored within an annulus of the atrium. The expandable prosthetic frame may be sized to be larger than the atrium. The sizing of the atrium may include identifying a center of an annulus of a side of a heart based on the image. The sizing of the atrium may include identifying a highest elevation point of the atrium based on the image. The highest elevation point may be highest relative to a plane corresponding to the annulus. The sizing of the atrium may include measuring a length between the highest elevation point and the center. The sizing of the atrium may include determining a point along the length intermediate between the highest elevation point and the center. The sizing of the atrium may include measuring a width of the atrium from an anterior margin to a posterior margin at the point along the length. The atrial implant may have an implant length that is within a range of between 5-30% greater than the length. The atrial implant may have an implant width that is within a range of between 5-30% greater than the width of the atrium.

The expandable prosthetic frame may include a prosthetic heart valve frame. The annular ring may include a prosthetic mitral valve frame. The expandable prosthetic frame may include an inner valve support configured to direct blood flow out of the implant toward a posterior of the heart when the atrial implant is deployed in the atrium.

The width may be measured parallel to the plane corresponding to the annulus. The width may be measured perpendicular to the length. The point at which the width is measured may be a midpoint along the length intermediate between the highest elevation point and the center of the annulus.

The second length and the second width of the implant may be greater by the same percentage. For example, the second length may be 15% greater than the length and the second width may be 15% greater than the width.

Apparatus and methods may include methods for sizing an atrial implant for implantation into an atrium on a side of a heart. The methods may include identifying a highest elevation point of the atrium on the side of a heart based on the image. The highest elevation point may be highest relative to a plane corresponding to an annulus of the first side of a heart. The methods may include determining a length between the highest elevation point and a first point on the plane. The methods may include determining a second point along the length intermediate between the highest elevation point and the first point. The methods may include measuring a width of the atrium from an anterior margin to a posterior margin at the second point along the length. The methods may include providing an implant having a second length that is within a range of between 5-30% greater than the length of the atrium. The methods may include providing an implant having a second width that is within a range of between 5-30% greater than the width of the atrium. The first point may be at a center of the annulus. The length may be determined by measuring the length between the highest elevation point and the center of the annulus.

Apparatus and methods may include methods for sizing an atrial implant for implantation into an atrium on a side of a heart. The methods may include identifying a highest elevation point of an atrium of the side of the heart based on the image. The highest elevation point may be highest relative to a plane corresponding to an annulus on the first side of the heart. The methods may include determining a length between the highest elevation point and a first point on the plane. The methods may include determining a second point along the length intermediate between the highest elevation point and the first point. The methods may include measuring a width of the atrium from an anterior margin to a posterior margin at the second point along the length.

Apparatus and methods may include an atrial implant. The implant may include an expandable prosthetic frame deployable within an atrium on a side of a heart. The implant may include an annular ring coupled to the expandable prosthetic frame to be anchored within an annulus of the atrium. The expandable prosthetic frame may be sized to be larger than the atrium. The frame may be sized by identifying a highest elevation point of the atrium based on the image. The highest elevation point may be highest relative to a plane corresponding to the annulus. The frame may be sized by measuring a length between the highest elevation point and a first point on the plane. The frame may be sized by determining a second point along the length intermediate between the highest elevation point and the first point. The frame may be sized by measuring a width of the atrium from an anterior margin to a posterior margin at the second point along the length. The implant may have an implant length that is within a range of between 5-30% greater than the length. The implant may have an implant width that is within a range of between 5-30% greater than the width of the atrium.

The steps of illustrative methods may be performed in an order other than the order shown and/or described herein. Some embodiments may omit steps shown and/or described in connection with the illustrative methods. Some embodiments may include steps that are neither shown nor described in connection with the illustrative methods. Illustrative method steps may be combined. For example, one illustrative method may include steps shown in connection with another illustrative method.

Some embodiments may omit features shown and/or described in connection with the illustrative apparatus. Some embodiments may include features that are neither shown nor described in connection with the illustrative apparatus. Features of illustrative apparatus may be combined. For example, one illustrative embodiment may include features shown in connection with another illustrative embodiment.

Embodiments may involve some or all of the features of the illustrative apparatus and/or some or all of the steps of the illustrative methods.

The illustrative apparatus and methods will now be described with reference to the accompanying Figures, which form a part hereof. It is to be understood that other embodiments may be utilized and that structural, functional and procedural modifications may be made without departing from the scope and spirit of the present disclosure.

FIG. 1 shows schematic view 100. Schematic view 100 may be a schematic view of a left side of a heart including atrium 101, ventricle 103 and aorta 105. The left side of the heart may include annulus 107 extending between atrium 101 and ventricle 103.

Plane 109 may represent an approximation of an upper annular surface of annulus 107. The approximation may be the level. Point 102 may be a midpoint of the upper annular surface. Point 102 may be on plane 109.

Schematic view 100 may include representative points used for measuring the length and the width. In schematic view 100, point 111 is selected as the point. Point 111 may be spaced apart from a highest point on a roof of atrium 101. Point 111 may be a highest point on a roof of atrium 101. A highest point on a roof of atrium 101 may be a point on the roof having a greatest vertical displacement from point 102.

Schematic view 100 illustrates point 113. Point 113 may be a point on the roof of atrium 101 that is vertically above point 102. Line 115 may extend between point 102 and point 113. Length 117 may be displaced at angle α away from line 115.

Width 123 may extend from a right side of atrium 101 to a left side of atrium 101. Width 123 may be parallel to plane 109. Width 123 may intersect point 119. Point 119 may be a midpoint of length 117. Point 119 may be positioned on the location of the length.

Width 121 may be perpendicular to length 117. Width 121 may intersect point 119.

Schematic view 100 may illustrate a schematic view of a left section of a CT scan image of a heart. The view may show a long axis view.

To size the implant for the left atrium, an annular surface, referred to alternately herein as a level, may be identified. To size the implant, a highest elevation point of the roof of the atrium shown in the image may be identified. To size the implant, a point adjacent the highest elevation point of the roof of the atrium shown in the image may be identified. The annular surface may be represented by a plane. The highest elevation point may be a highest location relative to the annular surface.

Length 117 between point 111 and point 102 may be measured. Point 119 along length 117 intermediate between point 111 and point 102 may be determined. Width 121 may be measured from an anterior margin to a posterior margin. Width 121 may intersect point 119.

The highest elevation point of the left atrium, referred to alternately herein as the highest anatomical point, may be generally located on an anterior side of the left atrium at an acute angle, such as angle α, which is counterclockwise relative to a vertical axis defined to extend between the center of the annulus to a roof of the left atrium vertically above the center (in FIG. 1, this is represented by line 115). Angle α may be, for example, within a range of 12-20 degrees or may be approximately within a range of 14-16 degrees, or angle α may be, for example, 16 degrees. In some people, angle α may be 0 degrees.

A width of the left atrium may be measured. The measurement may be performed in different ways. Width 123 of the left atrium may be measured parallel to plane 109. Width 121 may be measured perpendicular to length 117. Point 119 at which width 123 or width 121 is measured may be a midpoint along the length 117 intermediate between point 111 and the point 102.

The implant may be manufactured based on the measurements, such as, for example, length 117, and width 123 or width 121. The percentage at which a height of the implant is enlarged may differ from a percentage at which a maximum width of the implant is enlarged. The implant may be manufactured to be larger than the left atrium so that an ellipsoid defined by a curved portion of the implant has an ellipsoid height that is within a range of between 5-30% greater than length 117 and an ellipsoid width 123 or width 121 that is within a range of between 5-30% greater than the width 123 or width 121, respectively. The ellipsoid height and the ellipsoid width may alternatively be enlarged to each be within a narrower range such as between 5 to 25%, 5 to 20%, 5 to 15%, 5 to 10%, 10 to 25%, 10 to 20%, 10 to 15%, 15 to 30%, 15 to 25%, or 15 to 20%. In illustrative examples, the ellipsoid height and the ellipsoid width may be enlarged by approximately the same percentage. For example, the ellipsoid height may be 15% greater than length 117 and the ellipsoid width may be 15% greater than width 123 or width 121.

In determining which width to use for oversizing the implant, such as whether to use width 123 or width 121, both of these widths or other widths may be analyzed, such as by a computer, and a determination may be made as to which width will best fit the left atrium in which the implant is to be deployed. The determination may also be based on optimizing the blood flow.

The implant may be sized based on measurements of a heart in which the implant is to be implanted. The implant may be sized based at least in part on dimensions of the heart in which the implant is to be implanted.

The implant may include the annular ring near the bottom of the implant. The annular ring may fit within the annulus and hold the inner valve support to replace the native mitral valve. The annular ring may be manufactured such that, when the implant is deployed, the annular ring is oriented within the annulus such that there is an aorto-mitral angle β between the plane corresponding to the annulus and the aorta.

The aorto-mitral angle may be an angle between plane 109, which may approximate an upper annular surface of the annulus, and plane of aortic valve 125. Plane of aortic valve 125 may be determined by selecting points on the aortic annulus and determining a representative surface.

Angle β may be within a range of between 110 to 120 degrees rotated clockwise (downward) from the plane corresponding to the annulus. Angle β may be within a range of 112 to 115 degrees. Angle β may be approximately 114 degrees. This orientation of the annular ring with the mitral valve may serve to maintain a relatively normal blood flow. A large angle β may disengage an outflow of the mitral valve from inflow to the aortic valve because the valves are less crowded than if the angle β is a lower value, such as, for example, a value closer to 90°.

Figure 2:
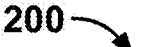
FIG. 2 shows illustrative methods in accordance with principles of the invention.
Figure 2:
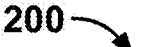

FIG. 2 shows illustrative image 200. Image 200 may include left ventricle 203, aorta 205 and atrium 201. Line 230 may be used to illustrate area 202 which, for measurement purposes described herein, may not be considered part of atrium 201.

Image 200 may define a cross-sectional plane. The cross-sectional plane may section a three-dimensional image of a left atrium along a long axis to generate image 200. Contour 206 may represent an intersection of the left atrium with the plane.

Image 200 may include level 207. Level 207 may include segment 208 extending across level 207 where the plane and level 207 intersect. Level 207 may include point 204. Point 204 may be a midpoint of segment 208. Point 204 may be positioned at the location on segment 208.

Image 200 may include representative points used for determining the length and the width. In image 200, highest point 209 is selected as the point. Highest point 209 may be a highest point on image 200. Highest point 209 may be a point on the contour of roof 210 having the greatest vertical displacement from point 204.

Image 200 illustrates point 211. Point 211 may be a point on roof 210 that is vertically above point 204. Line 215 may extend between point 211 and point 204. Line 215 may be displaced away from length 217 by angle 213.

Width 223 may extend from a right side of atrium 201 to a left side of atrium 201. Width 223 may be parallel to segment 208. Width 223 may be parallel to level 207. Width 223 may intersect point 219. Point 219 may be a midpoint of width 223. Point 219 may be positioned on the location of the length described herein.

Width 221 may be perpendicular to length 217. Width 221 may intersect point 219. One of widths 223 and 221 may be used to oversize the implant.

Figure 3:
FIG. 3 shows illustrative methods in accordance with principles of the invention.

FIG. 3 shows illustrative image 300. Image 300 may show the same anatomy that is shown in image 200. FIG. 3 shows point 307 being used for measuring length 301. Point 307 may be selected from range of points 303 positioned on the roof of atrium 201 which are spaced 0.5-2 cm away from highest point 209.

Figure 4:
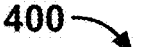
FIG. 4 shows illustrative methods in accordance with principles of the invention.

FIG. 4 shows illustrative image 400. Image 400 may show the same anatomy that is shown in image 200. FIG. 4 shows point 407 being used for measuring length 401. Point 407 may be selected from range of points 403 positioned on the roof of atrium 201 which are spaced 0-2 cm away from highest point 209.

Figure 5:
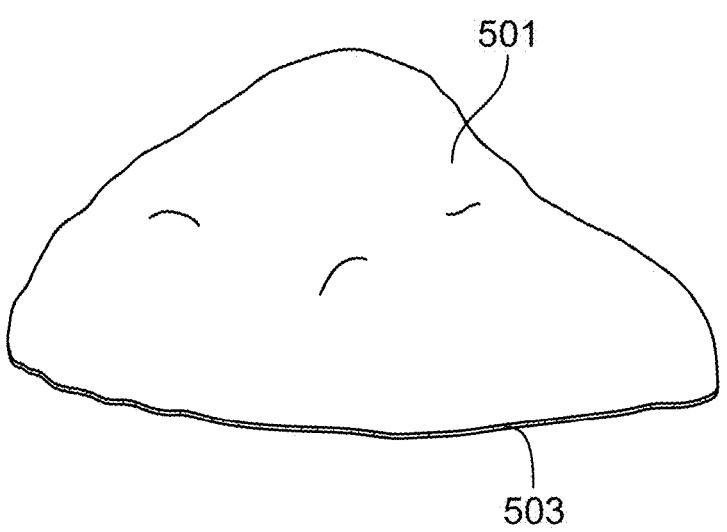
FIG. 5 shows illustrative methods in accordance with principles of the invention.

FIG. 5 shows a schematic cross-sectional view of level 500. The cross-sectional view of level 500 may define section 503. The cross-sectional view may include portion 501. Portion 501 may be a part of level 500 behind section 503 in the cross-sectional view. Section 503 may represent where level 500, and a cross-sectional plane used to generate the cross-sectional view, intersect.

Figure 6:
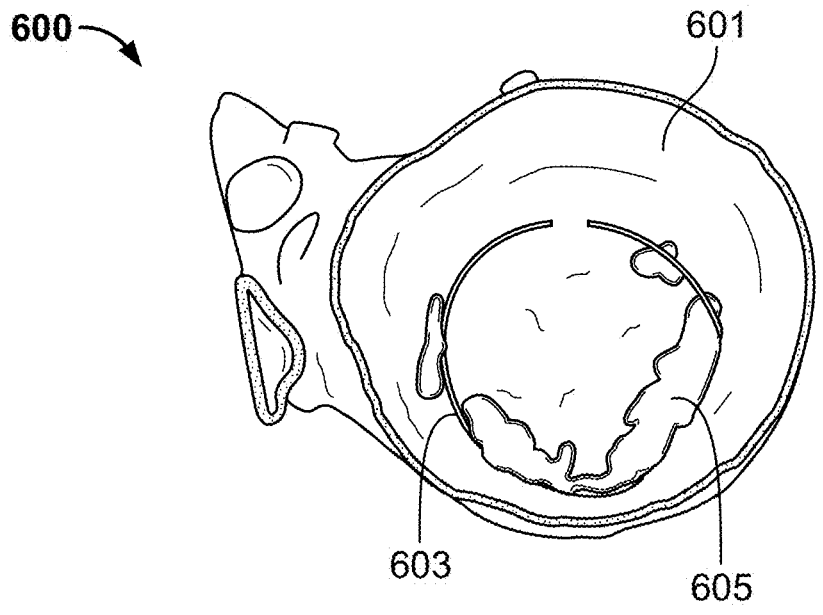
FIG. 6 shows illustrative methods in accordance with principles of the invention.

FIG. 6 shows top view 600 of a left atrium. Top view 600 includes left atrium 601, annulus 605 and spline 603. Spline 603 may be a computer-generated approximation of an upper surface of annulus 605. Spline 603 may be disc-shaped. The level may be a plane generated using spline 603.

Figure 7:
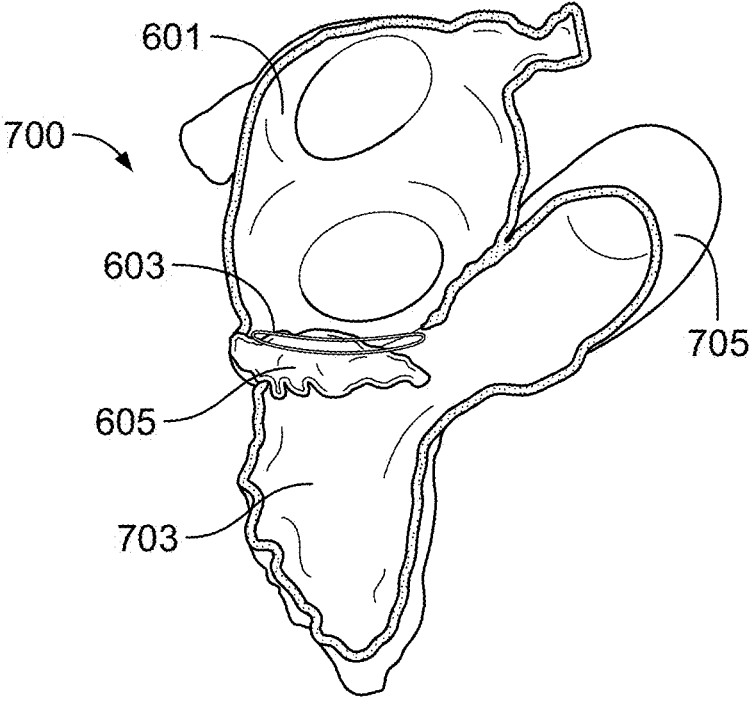
FIG. 7 shows illustrative methods in accordance with principles of the invention.

FIG. 7 shows a long axis view 700 of the left atrium illustrated in FIG. 6. Long axis view 700 may include ventricle 703 and aorta 705. Spline 603 is included on long axis view 700.

Figure 8:
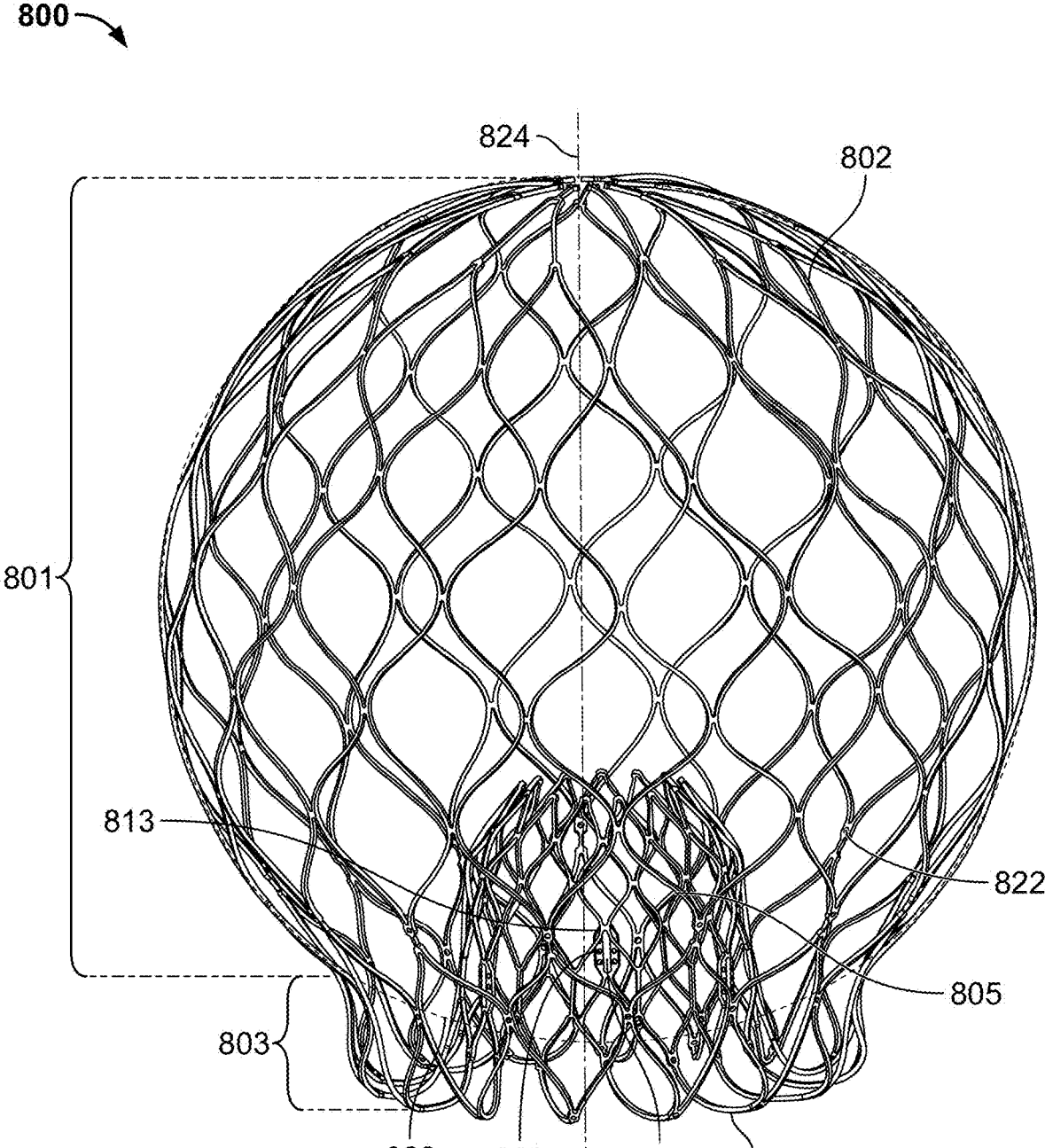
FIG. 8 shows illustrative apparatus in accordance with principles of the invention.

FIG. 8 shows illustrative implant 800. Axis 824 may be a central axis of implant 800.

Implant 800 may include curved portion 801. Implant 800 may be formed from cells 802. Implant 800 may include annular ring 803. Annular ring 803 may be covered with a covering (not shown). Annular ring 803 may extend away from curved portion 801. Ellipsoid 820 may be the ellipsoid conforming to curved portion 801.

Implant 800 may include transition section 807 and inner valve support 805. Implant 800 may include a hub (not shown) at a top of implant 800.

Cells of the implant may include an opening 822 for suturing the covering to the implant. Inner valve support 805 may include a plurality of leaflet extension attachment features ("LEAF") 813 for securing the leaflets to LEAF 813. LEAF 813 may include slot 826 for receiving ends of adjacent leaflets and holes 828 for suturing the leaflets to LEAF 813.

Figure 8A:
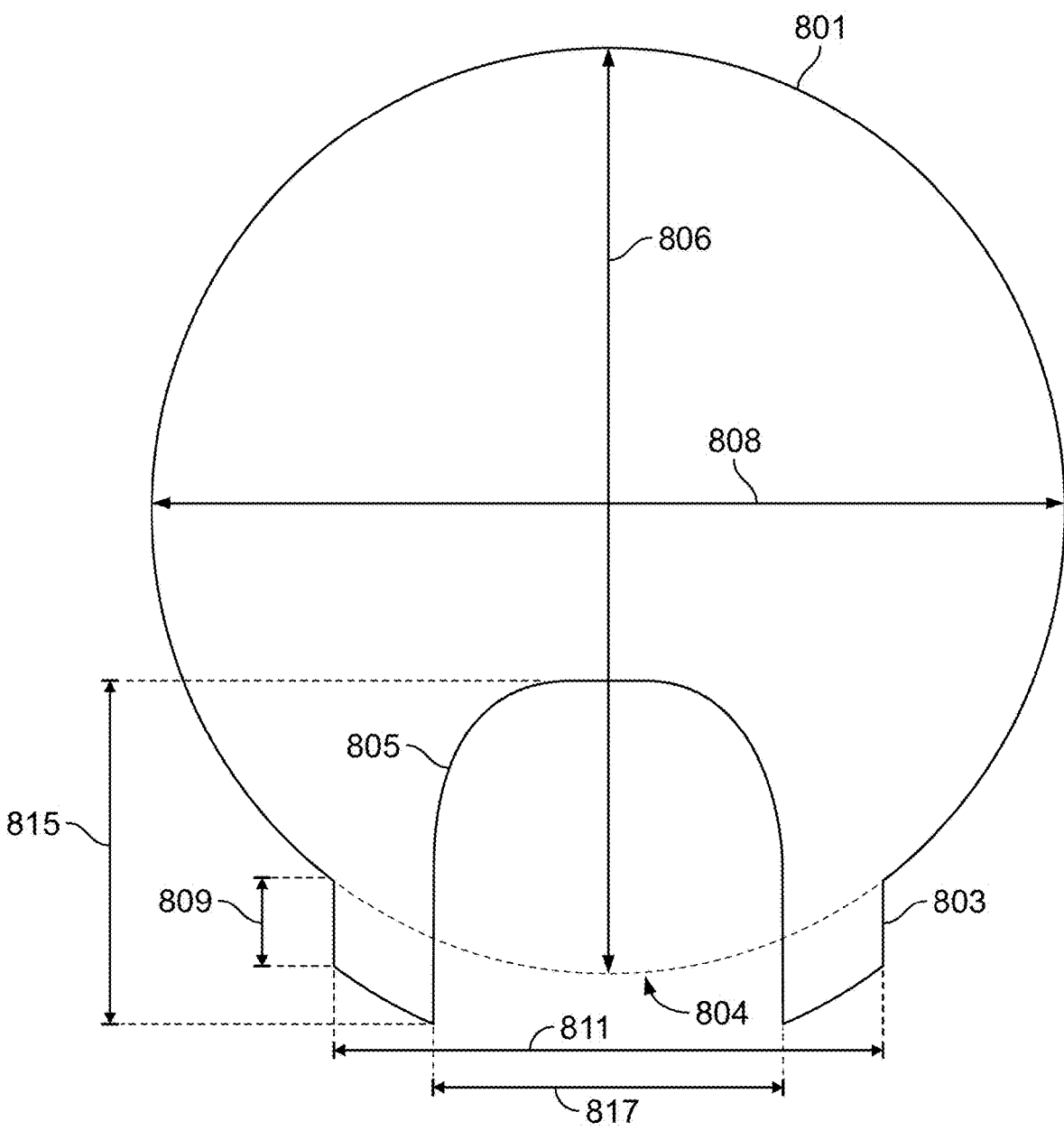
FIG. 8A shows illustrative apparatus and methods in accordance with principles of the invention.

FIG. 8A shows a schematic diagram of an outline of implant 800. FIG. 8A shows ellipse 804. Ellipse 804 may be a cross-section of ellipsoid 820. The cross-section may be taken along axis 824. FIG. 8A shows ellipse height 806 and ellipse width 808. FIG. 8A shows inner valve support height 815 and inner valve support width 817. FIG. 8A shows annular ring height 809 and annular ring width 811.

Ellipse height 806 may be a long axis of ellipse 804. Ellipse height 806 may be the ellipsoid height of ellipsoid 820. Ellipse height 806 may extend along axis 824. Ellipse width 808 may be a short axis of ellipse 804. Ellipse width 808 may be the ellipsoid width of ellipsoid 820. Illustrated heights and widths may be oversized as described herein.

Figure 9:
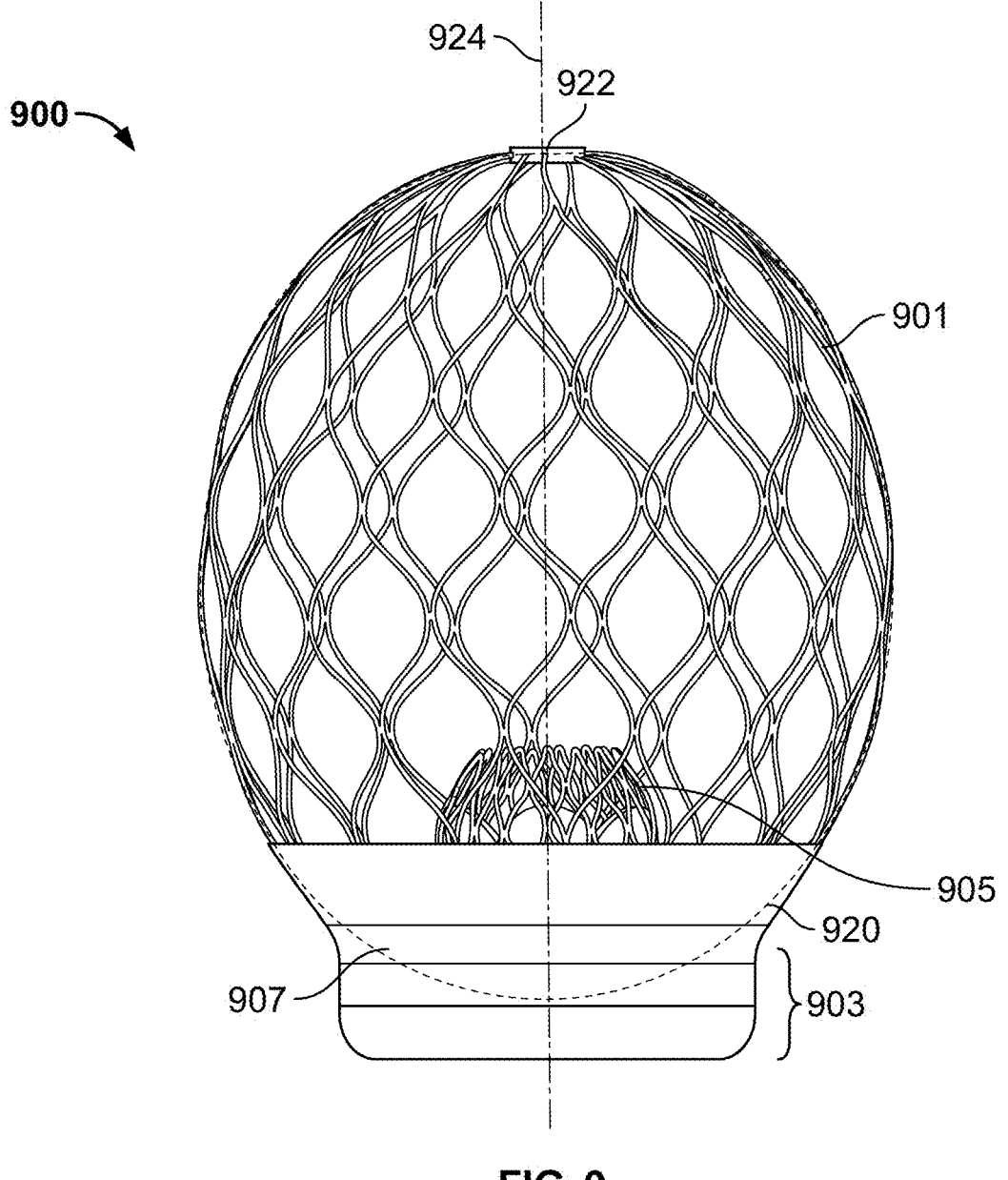
FIG. 9 shows illustrative apparatus in accordance with principles of the invention.

FIG. 9 shows illustrative implant 900. Axis 924 may be a central axis of implant 900. Implant 900 may include curved portion 901. Implant 900 may be formed from cells. Implant 900 may include annular ring 903. Annular ring 903 may be covered with covering 907. A bottom portion of curved portion 901 may also be covered by covering 907. Annular ring 903 may extend away from curved portion 901. Ellipsoid 920 may be the ellipsoid conforming to curved portion 901.

Implant 900 may include a transition section at a bottom of implant 900. Implant 900 may include inner valve support 905. Implant 900 may include hub 922. Hub 922 may be positioned at a top of implant 900. Ends of cells of implant 900 may be captured in hub 922 and configured to rotate within hub 922 to enable implant 900 to collapse and expand. Illustrated heights and widths may be oversized as described herein.

Figure 9A:
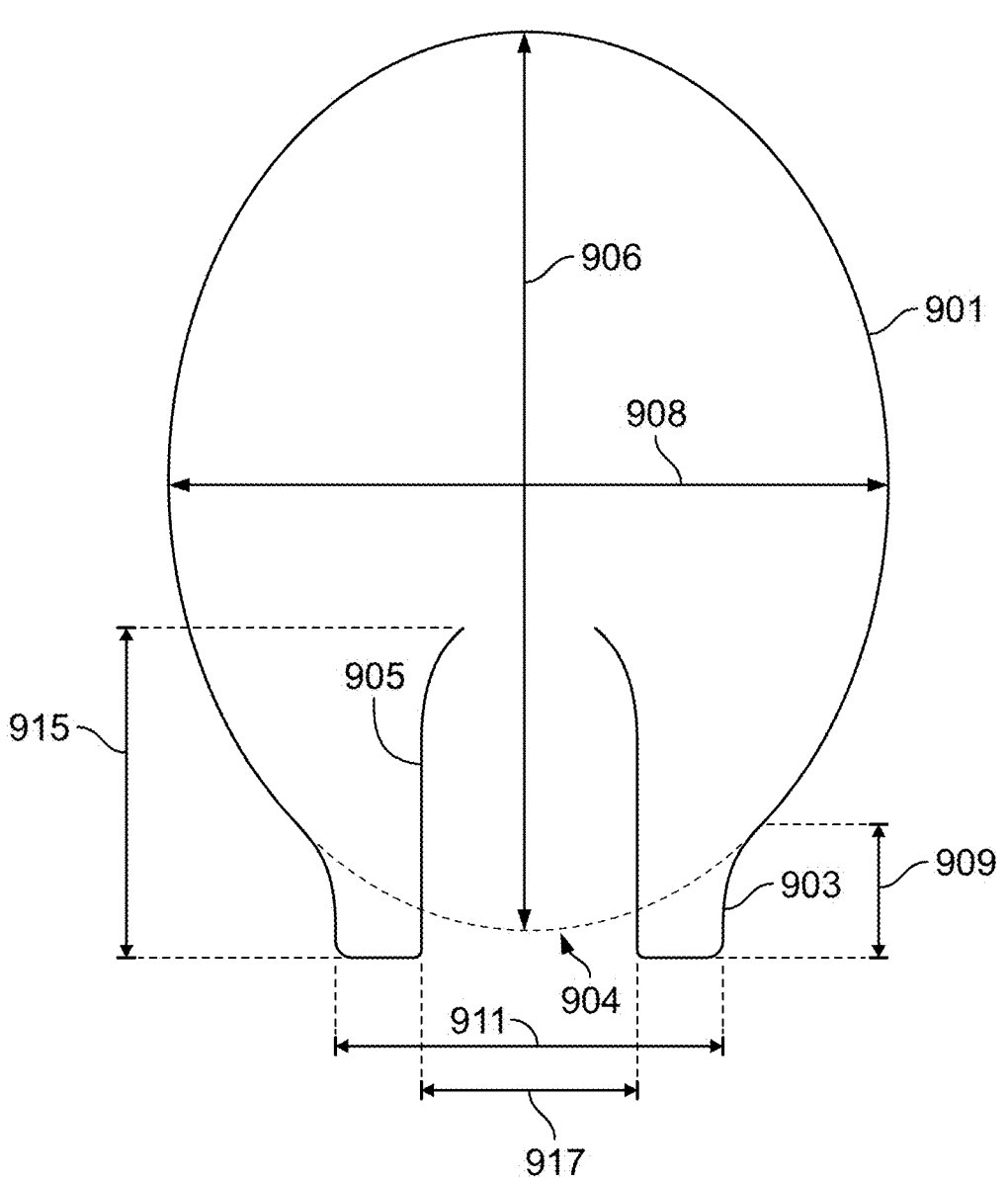
FIG. 9A shows illustrative apparatus and methods in accordance with principles of the invention.

FIG. 9A shows a schematic diagram of an outline of implant 900. FIG. 9A shows ellipse 904. Ellipse 904 may be a cross-section of ellipsoid 920. The cross-section may be taken along axis 924. FIG. 9A shows ellipse height 906 and ellipse width 908. FIG. 9A shows inner valve support height 915 and inner valve support width 917. FIG. 9A shows annular ring height 909 and annular ring width 911.

Ellipse height 906 may be a long axis of ellipse 904. Ellipse height 906 may be the ellipsoid height of ellipsoid 920. Ellipse height 906 may extend along axis 924. Ellipse width 908 may be a short axis of ellipse 904. Ellipse width 908 may be the ellipsoid width of ellipsoid 920.

Figure 10:
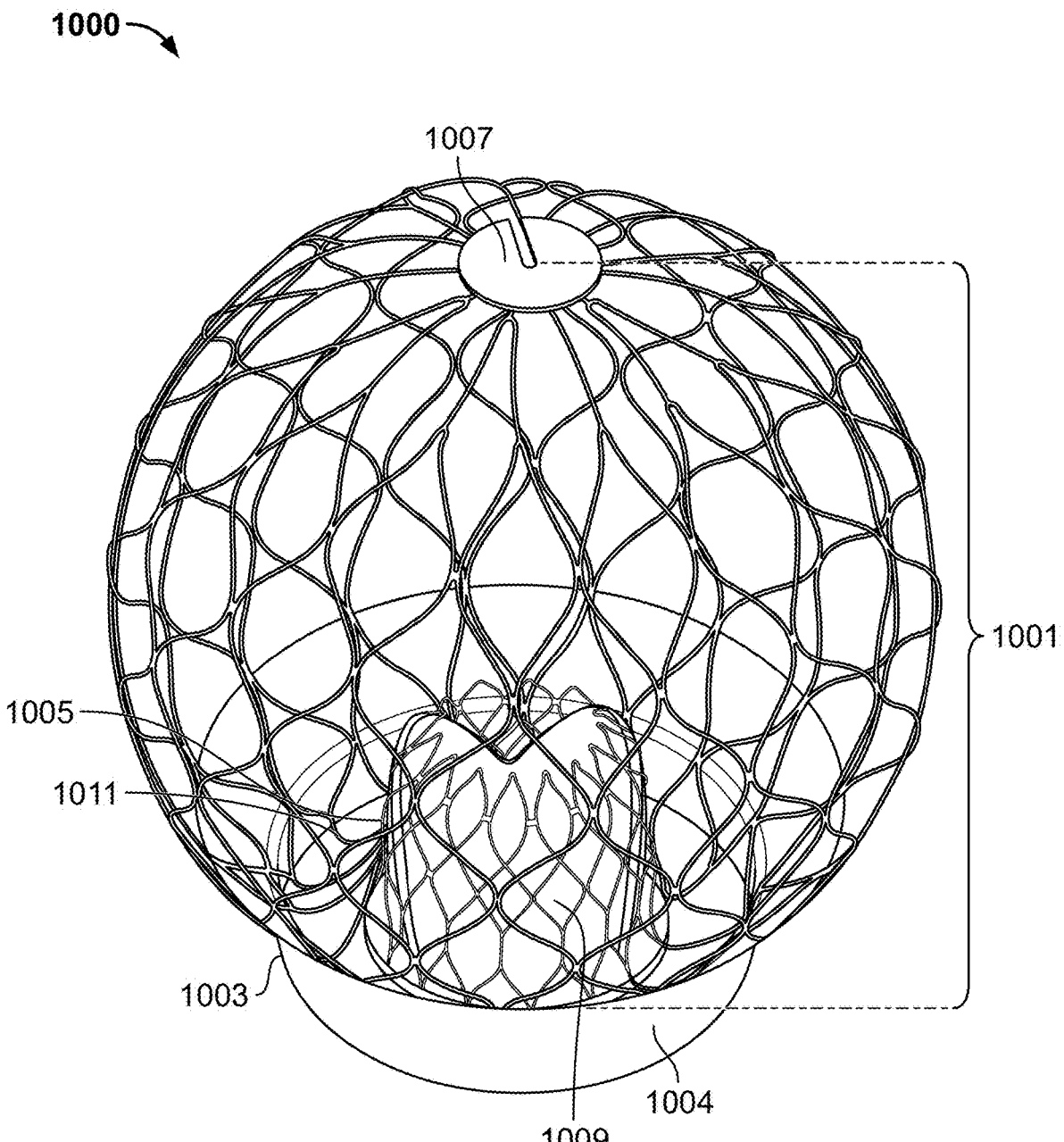
FIG. 10 shows illustrative apparatus in accordance with principles of the invention.

FIG. 10 shows illustrative implant 1000. Implant 1000 may include hub 1007. Hub 1007 may be positioned at a top of implant 1000.

Implant 1000 may include curved portion 1001. Implant 1000 may include annular ring 1003 covered with covering 1004. Covering 1004 may be formed from polyethylene terephthalate ("PET") or any other suitable medical fabric. Annular ring 1003 may extend away from curved portion 1001.

Curved portion 1001 and annular ring 1003 may together form an outer surface of implant 1000. Hub 1007 may also form the outer surface. As illustrated in FIG. 10, the outer surface may be an atraumatic surface that is not configured to pierce tissue when implant 1000 is deployed in a side of a heart.

Implant 1000 may include inner valve support 1005 supporting leaflets 1009.

Figure 11:
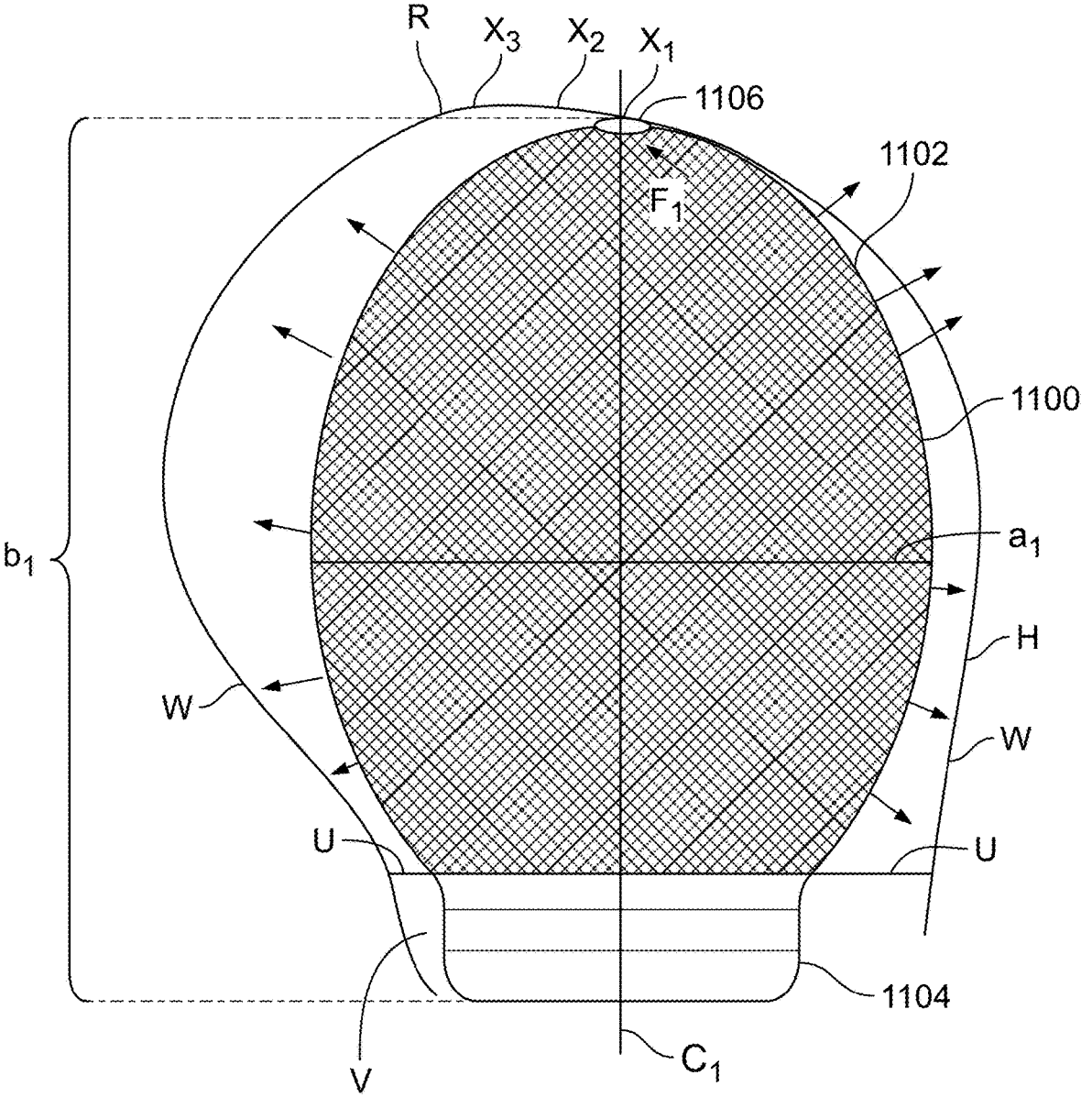
FIG. 11 shows illustrative apparatus and methods in accordance with principles of the invention.

Transition section 1011 may support inner valve support 1005 in an interior of implant 1000. FIG. 11 shows schematically illustrative implant 1100 in heart chamber H.

Implant 1100 may include curved portion 1102. Implant 1100 may include annular ring 1104. Implant 1100 may have an axis C ("C_i," at deployment stage i). Implant 1100 may include hub 1106.

Heart chamber H may include roof R, walls W, valve annulus V and upper annular surface U. Locations $X_1$, $X_2$ and $X_3$ may be locations on roof R corresponding to different stages of deployment of implant 1100. $X_3$ may have a height that is higher than $X_2$. $X_2$ may have a height that is higher than $X_1$.

The stages illustrated may be after release or partial release of implant 1100 from delivery instrumentation.

At a first stage of deployment axis $C_1$ may be aligned with location $X_1$. Axis $C_1$ may be normal or almost normal to upper annular surface U. Implant 1100 may have a width $a_1$. Implant 1100 may have a height $b_1$.

Implant 1100 may self-expand in a direction transverse to $C_1$. Implant 1100 may shrink in a direction parallel to $C_1$. Reactive forces against implant 1100 from one or both of wall W and roof R may result in a force $F_1$ that moves axis C into a position that is more aligned with a higher location, such as $X_2$ or $X_3$, on roof R. The reactive forces may result from the sizing methods shown and described herein.

Figure 12:
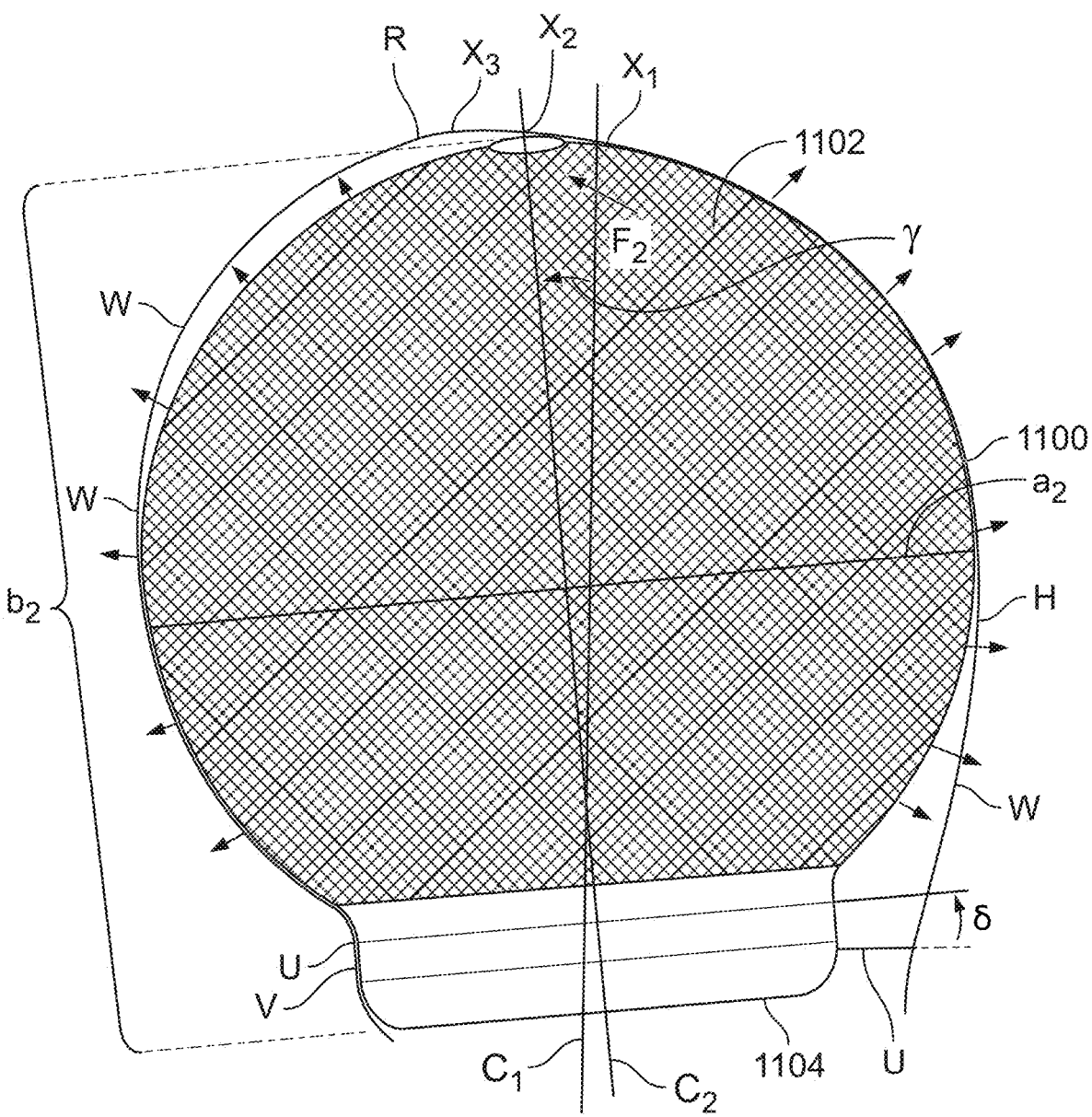
FIG. 12 shows illustrative apparatus and methods in accordance with principles of the invention.

FIG. 12 shows implant 1100 in a second stage of deployment. Axis C ("$C_2$") has rotated away from its previous orientation, $C_1$, by angle γ. $C_2$ is now aligned with location $X_2$ on roof R. Implant width a1 has increased to width az. Implant height b1 has been reduced to height $b_2$. Axis C is now oblique to upper annular surface U. Force $F_2$ may continue to urge axis C toward location $X_3$. When axis C reaches $X_3$, implant 1100 may be in a stable orientation relative to wall W. This may be because $X_3$ is the highest anatomical point on roof R, and thus if the orientation is perturbed, wall W may urge axis C back into alignment with location $X_3$. The alignment may result from the sizing methods shown and described herein. The overall pressure of one or both of wall W and roof R on implant 1100 may keep annular ring 1104 nested in valve annulus V. The different heights of roof R at locations such as $X_1$, $X_2$ and $X_3$, and similarly other points (not shown) opposite $X_1$ and $X_2$ on other sides of $X_3$ on roof R, may maintain annular ring 1104 at an angle δ from upper annular surface U. Maintenance of annular ring 1104 may result from the sizing methods shown and described herein.

Figure 13:
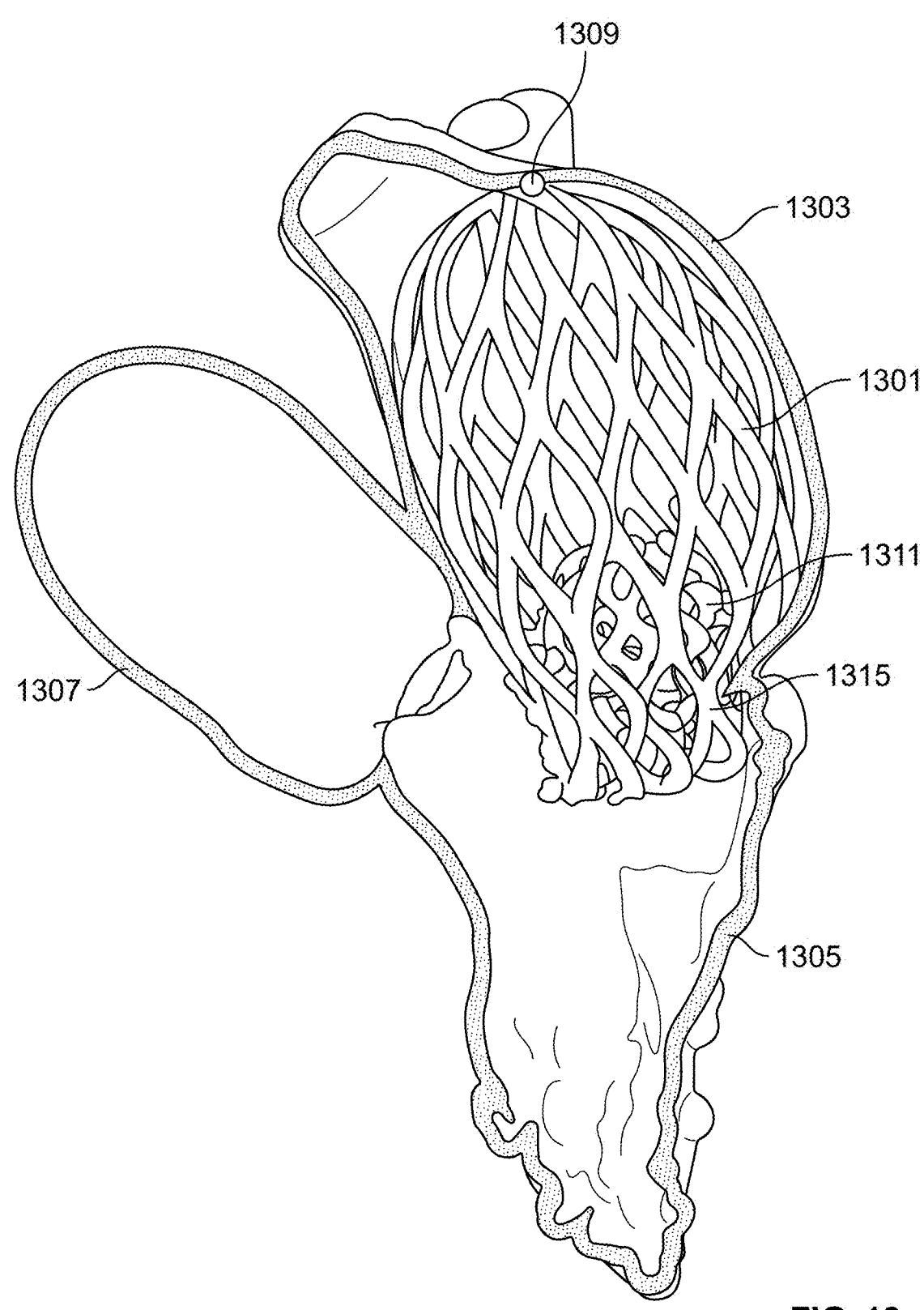
FIG. 13 shows illustrative apparatus and methods in accordance with principles of the invention.

FIG. 13 shows implant 1301 deployed in a left side of a heart. In FIG. 13 the side of the heart is shown in a cross-sectional view taken along a long axis. In FIG. 13, implant 1301 is not sectioned. The cross-sectional view includes aorta 1307.

Implant 1301 may have been sized using measurements of atrium 1303 such as the length and the width. Implant 1301 may have been sized using measurements of an annulus extending between atrium 1303 and ventricle 1305 such as the annular width.

Implant 1301 may be sized such that implant 1301, when deployed, is compressed within the left atrium. Implant 1301, when deployed, may contract and expand with atrium 1303 during the cardiac cycle.

A height of implant 1301, or a height of an ellipsoid conforming to a curved portion of implant 1301, may be oversized relative to the length of atrium 1303. This oversizing may ensure that implant 1301, when deployed, is seated in atrium 1303 such that top of implant 1301 sits at the highest anatomical point of the heart chamber. Implant 1301, when expanding, may move to position a top of the implant at highest anatomical point 1309.

This may align a central axis of implant 1301 with the central axis of the heart chamber. This may align a central axis of inner valve support 1311 with the central axis of the heart chamber. This may align the central axis of inner valve support 1311 with a central axis of the annulus. The alignment may be maintained during systole. The alignment may be maintained during diastole.

This positioning (e.g. at an angular orientation 213 illustrated in FIG. 2) may cause blood pumped from atrium 1303 to impinge upon posterior side of ventricle 1305, consistent with normal blood flow impingement in ventricle 1305. Consequently, the blood flow may be maintained in a relatively normal direction and pumped at a relatively normal rate.

The implant may include inner valve support 1311 pointing upward from an interior of annular ring 1315. Inner valve support 1311 may be configured to support and retain prosthetic valve leaflets (not shown). Inner valve support 1311 may direct blood flow to the posterior side of ventricle 1305. Inner valve support 1311 may be cylindrical. Inner valve support 1311 may be conical or partially conical.

A central axis of inner valve support 1311 may extend along a central axis of implant 1301.

A central axis of inner valve support 1311 may be oriented at an acute angle relative to the central axis of implant 1301.

Figure 14:
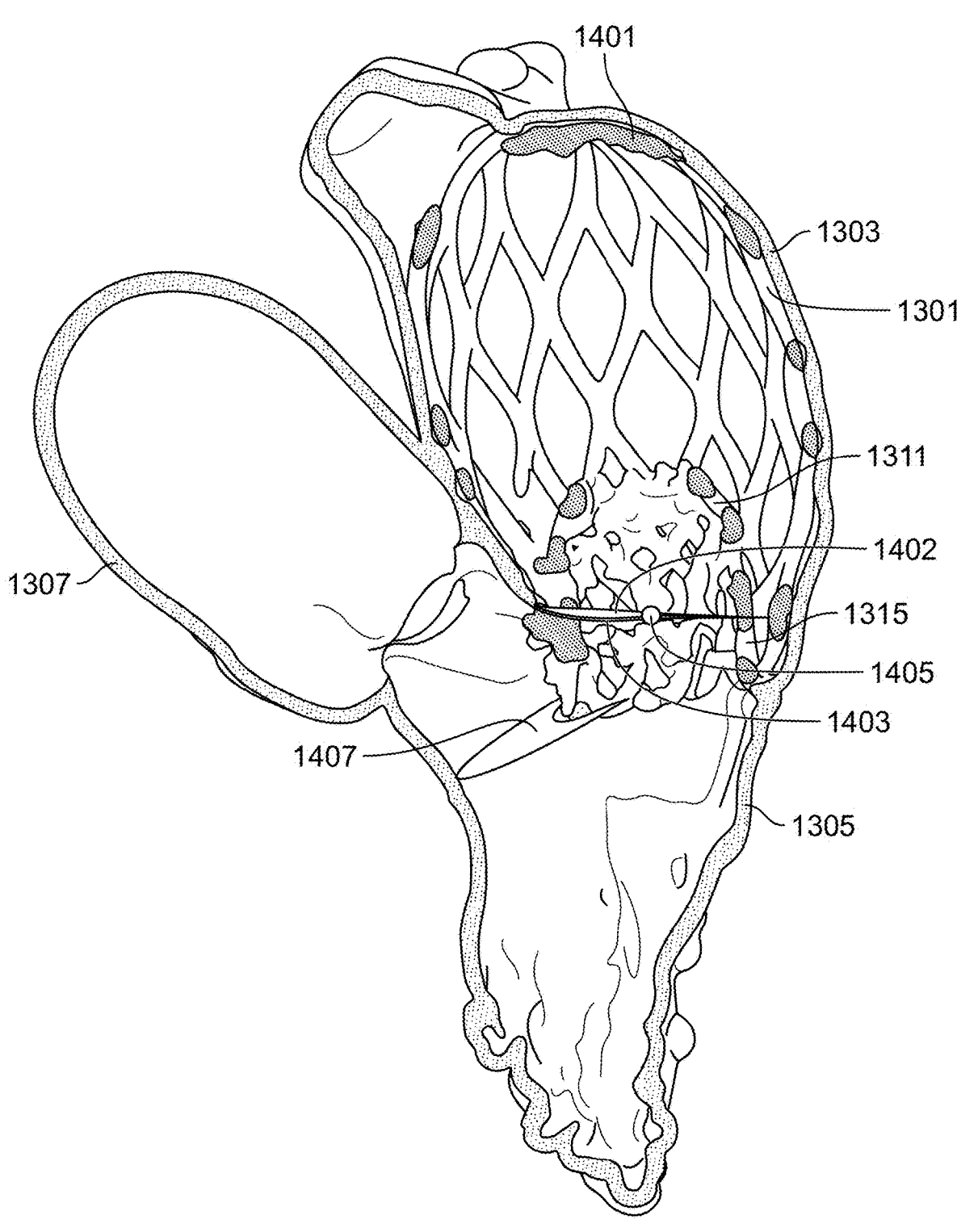
FIG. 14 shows illustrative apparatus and methods in accordance with principles of the invention.

FIG. 14 shows anatomy and apparatus illustrated in FIG. 13, where, in FIG. 14, implant 1301 is sectioned along the plane used to section the side of the heart. The plane may intersect implant 1301 to generate implant sections 1401.

In FIG. 14, level 1402 has been calculated to approximate an upper annular surface of an annulus extending between atrium 1303 and ventricle 1305 and overlaid on the image. Level 1402 may intersect the plane at segment 1403. Point 1405 may illustrate a midpoint of segment 1403.

FIG. 14 additionally illustrates left ventricular outflow tract ("LVOT") 1407. Annular ring 1315, during systole, may move away from LVOT 1407 to increase blood flow through LVOT 1407. Annular ring 1315, during systole, may move so as not to interfere with blood flowing through LVOT 1407.

Figure 15:
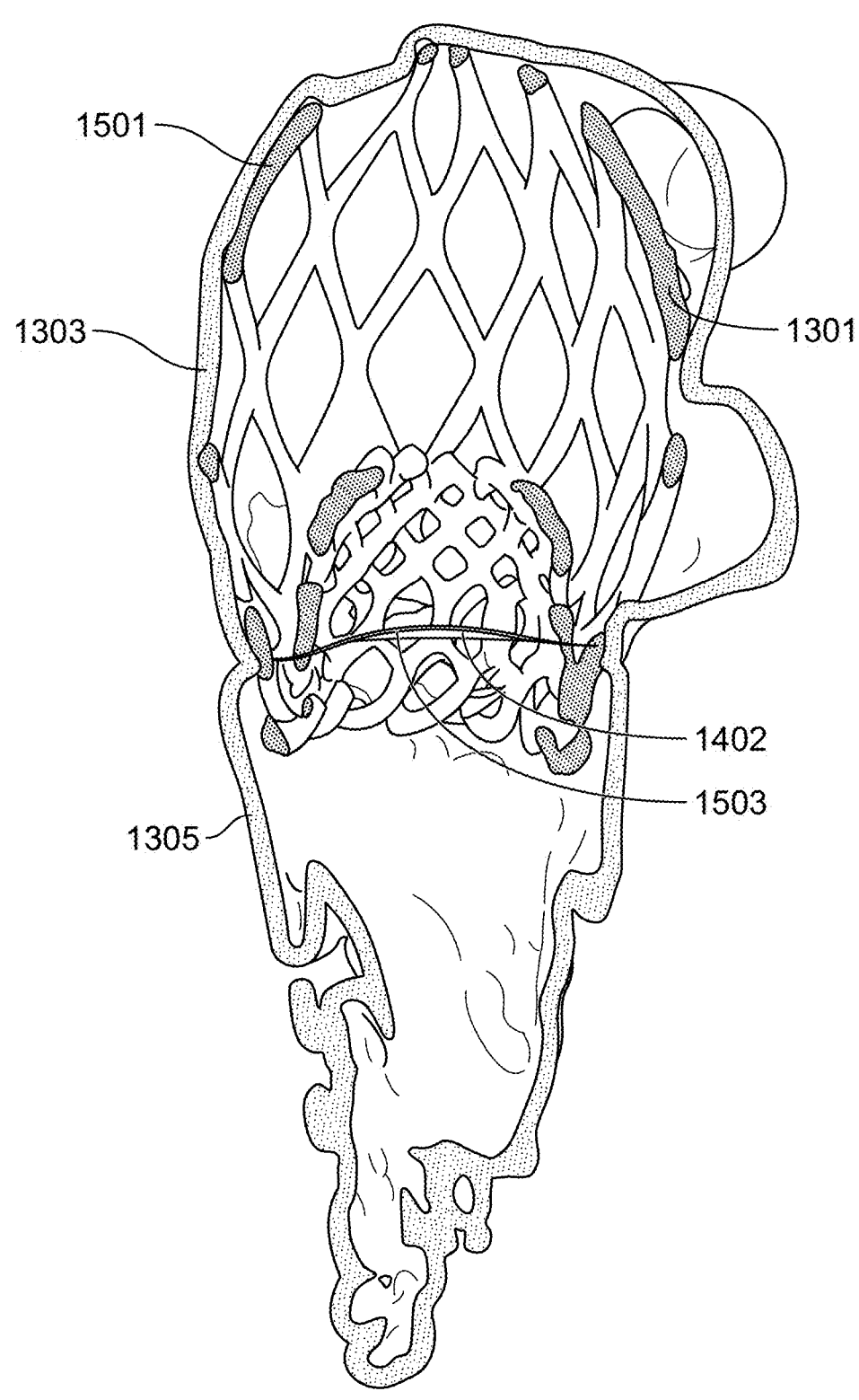
FIG. 15 shows illustrative apparatus and methods in accordance with principles of the invention.

FIG. 15 shows anatomy and apparatus illustrated in FIG. 13 in a cross-sectional view taken along a long axis. The plane may intersect implant 1301 to generate implant sections 1501. FIG. 15 includes level 1402. In FIG. 15, level 1402 intersects the sectioning plane at segment 1503.

All ranges and parameters disclosed herein shall be understood to encompass any and all subranges subsumed therein, every number between the endpoints, and the endpoints. For example, a stated range of "1 to 10" should be considered to include any and all subranges between (and inclusive of) the minimum value of 1 and the maximum value of 10; that is, all subranges beginning with a minimum value of 1 or more (e.g. 1 to 6.1), and ending with a maximum value of 10 or less (e.g., 2.3 to 10.4, 3 to 8, 4 to 7), and finally to each number 1, 2, 3, 4, 5, 6, 7, 8, 10, and 10 contained within the range.

Thus, apparatus and methods for a prosthetic heart valve have been provided. Persons skilled in the art will appreciate that the present invention may be practiced by other than the described embodiments, which are presented for purposes of illustration rather than of limitation.

The invention claimed is:

1. A method of manufacturing an implant for implantation in a heart chamber in a side of a heart, the method comprising forming a curved portion of the implant such that an ellipsoid conforming to the curved portion has:

an ellipsoid height that is greater than a length of the heart chamber by a percentage that is within a predetermined range of height percentage values; and an ellipsoid width that is greater than a width of the heart chamber by a percentage that is within a predetermined range of width percentage values;

wherein:

the length and width of the heart chamber are defined in an image of the heart chamber;

the length extends between:

a level corresponding to an upper annular surface at a bottom of the heart chamber; and a point that is:

on a roof of the heart chamber; and within 1.5 mm of a highest point on the roof in the image;

the method further comprises forming an annular ring of the implant, the forming the annular ring comprising the method steps of:

creating a first graphical model in which the ellipsoid has a first cell structure;

creating a second graphical model in which the annular ring has a first height and a second cell structure;

combining the first graphical model and the second graphical model such that the annular ring is positioned at a bottom of the ellipsoid;

determining that a height of the annular ring is below a threshold value;

increasing the first height to a second height; and forming the annular ring such that the annular ring has the second height.

2. The method of claim 1 further comprising:

selecting a first cell density of the implant when the ellipsoid height is less than a predetermined first value and the ellipsoid width is less than a predetermined second value; and selecting a second cell density of the implant when the ellipsoid height is greater than the predetermined first value and the ellipsoid width is greater than the predetermined second value.

3. The method of claim 1 wherein the threshold value is 10 mm.

4. The method of claim 1 wherein the point is the highest point on the roof in the image.

5. The method of claim 1 wherein the image includes a computed tomography (CT) scan image.

6. The method of claim 1 wherein:

the image has a scale that relates a dimension of the image to a corresponding dimension of the heart chamber; and the length and width are measured on the image.

7. The method of claim 1 wherein the image is a cross-sectional view of the heart chamber taken along an apical long axis of the heart chamber.

8. The method of claim 7 wherein:

the side of the heart is a left side of the heart; and the cross-sectional view passes through a center of a mitral valve orifice and a left ventricular apex.

9. The method of claim 1 wherein:

the heart chamber is a left atrium; and the roof of the heart chamber is within 0.5-1.5 mm of a bifurcation of a pulmonary trunk and a right pulmonary artery.

10. The method of claim 1 wherein:

the heart chamber is a right atrium; and the roof of the heart chamber is a surface parallel to an interatrial septum and spaced vertically above a tricuspid annulus at a superior atrial wall.

11. The method of claim 1 wherein the level is a three-dimensional approximation of the upper annular surface.

12. The method of claim 11 wherein:

the image defines a cross-sectional plane;

an intersection of the level with the plane defines a segment; and the length extends between:

the segment; and the point.

13. The method of claim 12 wherein the length extends between:

a midpoint of the segment; and the point.

14. The method of claim 13 wherein:

an intersection of the heart chamber with the plane defines a contour; and the point and the highest point are on the contour.

15. The method of claim 14 wherein an acute angle is defined between:

a line extending from the midpoint to the highest point; and a vertical axis extending from the midpoint to a top of the contour vertically above the midpoint.

16. The method of claim 1 further comprising forming the implant from a superelastic material such that an outer face of the implant is an atraumatic surface and the implant is collapsible for deployment into the heart chamber and thereafter expandable such that the implant:

is anchorable within the heart chamber by pressured contact with the heart chamber; and does not pierce heart tissue.

17. The method of claim 16 wherein the curved portion, when expanding in the heart chamber, undergoes movement in response to pressure from walls of the heart chamber, wherein the movement converges an implant axis with a central axis of the heart chamber.

18. The method of claim 17 wherein the central axis of the heart chamber:

extends through a highest anatomical point of the heart chamber; and is oblique relative to a vertical axis extending from a midpoint of the level to a top of the heart chamber vertically above the midpoint.

19. The method of claim 17 wherein the movement is absent a force applied by an instrument.

20. The method of claim 19 wherein the movement is driven by an expansion force of the curved portion and a shape of the heart chamber.

21. The method of claim 17 wherein the implant axis is a central axis of the implant.

22. The method of claim 17 wherein the implant axis extends along a central axis of the curved portion.

23. The method of claim 17 wherein the movement positions a top of the implant at a highest anatomical point of the heart chamber.

24. The method of claim 17 wherein the movement positions a hub of the implant at a highest anatomical point of the heart chamber.

25. The method of claim 24 wherein the movement does not occur when the implant axis is aligned with a central axis of the heart chamber.

26. The method of claim 17 wherein the forming the annular ring further comprises forming an annular ring extending away from the curved portion, the annular ring being sized to be anchored in an annulus of the side of the heart, the annulus defining the upper annular surface, wherein:

the movement aligns an annular ring central axis with the central axis of the heart chamber.

27. The method of claim 26 wherein the curved portion maintains alignment of the annular ring central axis with the central axis of the heart chamber during a heart cycle.

28. The method of claim 27 wherein:

the heart chamber is an atrium and the side of the heart includes a ventricle; and the alignment of the annular ring central axis with the central axis of the heart chamber during systole provides blood flow impingement on a posterior side of the ventricle.

29. A method of manufacturing an implant for implantation in a heart chamber in a side of a heart, the method comprising forming a curved portion of the implant such that an ellipsoid conforming to the curved portion has:

an ellipsoid height that is greater than a length of the heart chamber by a percentage that is within a predetermined range of height percentage values; and an ellipsoid width that is greater than a width of the heart chamber by a percentage that is within a predetermined range of width percentage values;

wherein:

the length and width of the heart chamber are defined in an image of the heart chamber;

the length extends between:

a level corresponding to an upper annular surface at a bottom of the heart chamber; and a point that is:

on a roof of the heart chamber; and within 1.5 mm of a highest point on the roof in the image; and the method further comprises:

selecting a first cell density of the implant when the ellipsoid height is less than a predetermined first value and the ellipsoid width is less than a predetermined second value; and selecting a second cell density of the implant when the ellipsoid height is greater than the predetermined first value and the ellipsoid width is greater than the predetermined second value.

30. The method of claim 29 further comprising:

creating a first graphical model in which the ellipsoid has a first cell structure;

creating a second graphical model of an annular ring having a first height and a second cell structure;

combining the first graphical model and the second graphical model such that the annular ring is positioned at a bottom of the ellipsoid;

determining that a height of the annular ring is below a threshold value;

increasing the first height to a second height; and forming the annular ring such that the annular ring has the second height;

wherein:

the threshold value is 10 mm.

31. The method of claim 29 wherein the point is the highest point on the roof in the image.

32. The method of claim 29 wherein the image includes a computed tomography (CT) scan image.

33. The method of claim 29 wherein:

the image has a scale that relates a dimension of the image to a corresponding dimension of the heart chamber; and the length and width are measured on the image.

34. The method of claim 29 wherein the image is a cross-sectional view of the heart chamber taken along an apical long axis of the heart chamber.

35. The method of claim 34 wherein:
the side of the heart is a left side of the heart; and
the cross-sectional view passes through a center of a mitral valve orifice and a left ventricular apex.

36. The method of claim 29 wherein:
the heart chamber is a left atrium; and
the roof of the heart chamber is within 0.5-1.5 mm of a bifurcation of a pulmonary trunk and a right pulmonary artery.

37. The method of claim 29 wherein:
the heart chamber is a right atrium; and
the roof of the heart chamber is a surface parallel to an interatrial septum and spaced vertically above a tricuspid annulus at a superior atrial wall.

38. The method of claim 29 wherein the level is a three-dimensional approximation of the upper annular surface.

39. The method of claim 38 wherein:
the image defines a cross-sectional plane;
an intersection of the level with the plane defines a segment; and
the length extends between:
the segment; and
the point.

40. The method of claim 39 wherein the length extends between:
a midpoint of the segment; and
the point.

41. The method of claim 40 wherein:
an intersection of the heart chamber with the plane defines a contour; and
the point and the highest point are on the contour.

42. The method of claim 41 wherein an acute angle is defined between:
a line extending from the midpoint to the highest point; and
a vertical axis extending from the midpoint to a top of the contour vertically above the midpoint.

43. The method of claim 29 further comprising forming the implant from a superelastic material such that an outer face of the implant is an atraumatic surface and the implant is collapsible for deployment into the heart chamber and thereafter expandable such that the implant:
is anchorable within the heart chamber by pressured contact with the heart chamber; and
does not pierce heart tissue.

44. The method of claim 43 wherein the curved portion, when expanding in the heart chamber, undergoes movement in response to pressure from walls of the heart chamber, wherein the movement converges an implant axis with a central axis of the heart chamber.

45. The method of claim 44 wherein the central axis of the heart chamber:
extends through a highest anatomical point of the heart chamber; and
is oblique relative to a vertical axis extending from a midpoint of the level to a top of the heart chamber vertically above the midpoint.

46. The method of claim 44 wherein the movement is move absent a force applied by an instrument.

47. The method of claim 46 wherein the movement is driven by an expansion force of the curved portion and a shape of the heart chamber.

48. The method of claim 44 wherein the implant axis is a central axis of the implant.

49. The method of claim 44 wherein the implant axis extends along a central axis of the curved portion.

50. The method of claim 44 wherein the movement positions a top of the implant at a highest anatomical point of the heart chamber.

51. The method of claim 44 wherein the movement positions a hub of the implant at a highest anatomical point of the heart chamber.

52. The method of claim 51 wherein the movement does not occur when the implant axis is aligned with a central axis of the heart chamber.

53. The method of claim 44 further comprising forming an annular ring extending away from the curved portion, the annular ring being sized to be anchored in an annulus of the side of the heart, the annulus defining the upper annular surface, wherein:
the movement aligns an annular ring central axis with the central axis of the heart chamber.

54. The method of claim 53 wherein the curved portion maintains alignment of the annular ring central axis with the central axis of the heart chamber during a heart cycle.

55. The method of claim 54 wherein:
the heart chamber is an atrium and the side of the heart includes a ventricle; and
the alignment of the annular ring central axis with the central axis of the heart chamber during systole provides blood flow impingement on a posterior side of the ventricle.

56. A method of manufacturing an implant for implantation in a heart chamber in a side of a heart, the method comprising forming a curved portion of the implant such that an ellipsoid conforming to the curved portion has:
an ellipsoid height that is greater than a length of the heart chamber by a percentage that is within a predetermined range of height percentage values; and
an ellipsoid width that is greater than a width of the heart chamber by a percentage that is within a predetermined range of width percentage values;
wherein:
the length and width of the heart chamber are defined in an image of the heart chamber;
the length extends between:
a level corresponding to an upper annular surface at a bottom of the heart chamber; and
a point that is:
on a roof of the heart chamber; and
within 1.5 mm of a highest point on the roof in the image; and
the image includes a computed tomography (CT) scan image.

57. The method of claim 56 further comprising:
creating a first graphical model in which the ellipsoid has a first cell structure;
creating a second graphical model of an annular ring having a first height and a second cell structure;
combining the first graphical model and the second graphical model such that the annular ring is positioned at a bottom of the ellipsoid;
determining that a height of the annular ring is below a threshold value;
increasing the first height to a second height; and
forming the annular ring such that the annular ring has the second height;
wherein:
the threshold value is 10 mm.

58. The method of claim 56 wherein the point is the highest point on the roof in the image.

59. The method of claim 56 wherein:

the image has a scale that relates a dimension of the image to a corresponding dimension of the heart chamber; and the length and width are measured on the image.

60. The method of claim 56 wherein the image is a cross-sectional view of the heart chamber taken along an apical long axis of the heart chamber.

61. The method of claim 60 wherein:

the side of the heart is a left side of the heart; and the cross-sectional view passes through a center of a mitral valve orifice and a left ventricular apex.

62. The method of claim 56 wherein:

the heart chamber is a left atrium; and the roof of the heart chamber is within 0.5-1.5 mm of a bifurcation of a pulmonary trunk and a right pulmonary artery.

63. The method of claim 56 wherein:

the heart chamber is a right atrium; and the roof of the heart chamber is a surface parallel to an interatrial septum and spaced vertically above a tricuspid annulus at a superior atrial wall.

64. The method of claim 56 wherein the level is a three-dimensional approximation of the upper annular surface.

65. The method of claim 64 wherein:

the image defines a cross-sectional plane;

an intersection of the level with the plane defines a segment; and the length extends between:

the segment; and the point.

66. The method of claim 65 wherein the length extends between:

a midpoint of the segment; and the point.

67. The method of claim 66 wherein:

an intersection of the heart chamber with the plane defines a contour; and the point and the highest point are on the contour.

68. The method of claim 67 wherein an acute angle is defined between:

a line extending from the midpoint to the highest point; and a vertical axis extending from the midpoint to a top of the contour vertically above the midpoint.

69. The method of claim 56 further comprising forming the implant from a superelastic material such that an outer face of the implant is an atraumatic surface and the implant is collapsible for deployment into the heart chamber and thereafter expandable such that the implant:

is anchorable within the heart chamber by pressured contact with the heart chamber; and does not pierce heart tissue.

70. The method of claim 69 wherein the curved portion, when expanding in the heart chamber, undergoes movement in response to pressure from walls of the heart chamber, wherein the movement converges an implant axis with a central axis of the heart chamber.

71. The method of claim 70 wherein the central axis of the heart chamber:

extends through a highest anatomical point of the heart chamber; and is oblique relative to a vertical axis extending from a midpoint of the level to a top of the heart chamber vertically above the midpoint.

72. The method of claim 70 wherein the movement is absent a force applied by an instrument.

73. The method of claim 72 wherein the movement is driven by an expansion force of the curved portion and a shape of the heart chamber.

74. The method of claim 70 wherein the implant axis is a central axis of the implant.

75. The method of claim 70 wherein the implant axis extends along a central axis of the curved portion.

76. The method of claim 70 wherein the movement positions a top of the implant at a highest anatomical point of the heart chamber.

77. The method of claim 70 wherein the movement positions a hub of the implant at a highest anatomical point of the heart chamber.

78. The method of claim 77 wherein the movement does not occur when the implant axis is aligned with a central axis of the heart chamber.

79. The method of claim 70 further comprising forming an annular ring extending away from the curved portion, the annular ring being sized to be anchored in an annulus of the side of the heart, the annulus defining the upper annular surface, wherein:

the movement aligns an annular ring central axis with the central axis of the heart chamber.

80. The method of claim 79 wherein the curved portion maintains alignment of the annular ring central axis with the central axis of the heart chamber during a heart cycle.

81. The method of claim 80 wherein:

the heart chamber is an atrium and the side of the heart includes a ventricle; and the alignment of the annular ring central axis with the central axis of the heart chamber during systole provides blood flow impingement on a posterior side of the ventricle.

82. A method of manufacturing an implant for implantation in a heart chamber in a side of a heart, the method comprising forming a curved portion of the implant such that an ellipsoid conforming to the curved portion has:

an ellipsoid height that is greater than a length of the heart chamber by a percentage that is within a predetermined range of height percentage values; and an ellipsoid width that is greater than a width of the heart chamber by a percentage that is within a predetermined range of width percentage values;

wherein:

the length and width of the heart chamber are defined in an image of the heart chamber;

the length extends between:

a level corresponding to an upper annular surface at a bottom of the heart chamber; and a point that is:

on a roof of the heart chamber; and within 1.5 mm of a highest point on the roof in the image;

the image has a scale that relates a dimension of the image to a corresponding dimension of the heart chamber; and the length and width are measured on the image.

83. The method of claim 82 further comprising:

creating a first graphical model in which the ellipsoid has a first cell structure;

creating a second graphical model of an annular ring having a first height and a second cell structure;

combining the first graphical model and the second graphical model such that the annular ring is positioned at a bottom of the ellipsoid;

determining that a height of the annular ring is below a threshold value;

increasing the first height to a second height; and forming the annular ring such that the annular ring has the second height;

wherein:

the threshold value is 10 mm.

84. The method of claim 82 wherein the point is the highest point on the roof in the image.

85. The method of claim 82 wherein the image is a cross-sectional view of the heart chamber taken along an apical long axis of the heart chamber.

86. The method of claim 85 wherein:

the side of the heart is a left side of the heart; and the cross-sectional view passes through a center of a mitral valve orifice and a left ventricular apex.

87. The method of claim 82 wherein:

the heart chamber is a left atrium; and the roof of the heart chamber is within 0.5-1.5 mm of a bifurcation of a pulmonary trunk and a right pulmonary artery.

88. The method of claim 82 wherein:

the heart chamber is a right atrium; and the roof of the heart chamber is a surface parallel to an interatrial septum and spaced vertically above a tricuspid annulus at a superior atrial wall.

89. The method of claim 82 wherein the level is a three-dimensional approximation of the upper annular surface.

90. The method of claim 89 wherein:

the image defines a cross-sectional plane;

an intersection of the level with the plane defines a segment; and the length extends between:

the segment; and the point.

91. The method of claim 90 wherein the length extends between:

a midpoint of the segment; and the point.

92. The method of claim 91 wherein:

an intersection of the heart chamber with the plane defines a contour; and the point and the highest point are on the contour.

93. The method of claim 92 wherein an acute angle is defined between:

a line extending from the midpoint to the highest point; and a vertical axis extending from the midpoint to a top of the contour vertically above the midpoint.

94. The method of claim 82 further comprising forming the implant from a superelastic material such that an outer face of the implant is an atraumatic surface and the implant is collapsible for deployment into the heart chamber and thereafter expandable such that the implant:

is anchorable within the heart chamber by pressured contact with the heart chamber; and does not pierce heart tissue.

95. The method of claim 94 wherein the curved portion, when expanding in the heart chamber, undergoes movement in response to pressure from walls of the heart chamber, wherein the movement converges an implant axis with a central axis of the heart chamber.

96. The method of claim 95 wherein the central axis of the heart chamber:

extends through a highest anatomical point of the heart chamber; and is oblique relative to a vertical axis extending from a midpoint of the level to a top of the heart chamber vertically above the midpoint.

97. The method of claim 95 wherein the movement is absent a force applied by an instrument.

98. The method of claim 97 wherein the movement is driven by an expansion force of the curved portion and a shape of the heart chamber.

99. The method of claim 95 wherein the implant axis is a central axis of the implant.

100. The method of claim 95 wherein the implant axis extends along a central axis of the curved portion.

101. The method of claim 95 wherein the movement positions a top of the implant at a highest anatomical point of the heart chamber.

102. The method of claim 95 wherein the movement positions a hub of the implant at a highest anatomical point of the heart chamber.

103. The method of claim 102 wherein the movement does not occur when the implant axis is aligned with a central axis of the heart chamber.

104. The method of claim 95 further comprising forming an annular ring extending away from the curved portion, the annular ring being sized to be anchored in an annulus of the side of the heart, the annulus defining the upper annular surface, wherein:

the movement aligns an annular ring central axis with the central axis of the heart chamber.

105. The method of claim 104 wherein the curved portion maintains alignment of the annular ring central axis with the central axis of the heart chamber during a heart cycle.

106. The method of claim 105 wherein:

the heart chamber is an atrium and the side of the heart includes a ventricle; and the alignment of the annular ring central axis with the central axis of the heart chamber during systole provides blood flow impingement on a posterior side of the ventricle.

107. A method of manufacturing an implant for implantation in a heart chamber in a side of a heart, the method comprising forming a curved portion of the implant such that an ellipsoid conforming to the curved portion has:

an ellipsoid height that is greater than a length of the heart chamber by a percentage that is within a predetermined range of height percentage values; and an ellipsoid width that is greater than a width of the heart chamber by a percentage that is within a predetermined range of width percentage values;

wherein:

the length and width of the heart chamber are defined in an image of the heart chamber;

the length extends between:

a level corresponding to an upper annular surface at a bottom of the heart chamber; and a point that is:

on a roof of the heart chamber; and within 1.5 mm of a highest point on the roof in the image;

the level is a three-dimensional approximation of the upper annular surface;

the image defines a cross-sectional plane;

an intersection of the level with the plane defines a segment;

the length extends between:

a midpoint of the segment; and the point;

an intersection of the heart chamber with the plane defines a contour;

the point and the highest point are on the contour; and an acute angle is defined between:

a line extending from the midpoint to the highest point; and a vertical axis extending from the midpoint to a top of the contour vertically above the midpoint.

108. The method of claim 107 further comprising:

creating a first graphical model in which the ellipsoid has a first cell structure;

creating a second graphical model of an annular ring having a first height and a second cell structure;

combining the first graphical model and the second graphical model such that the annular ring is positioned at a bottom of the ellipsoid;

determining that a height of the annular ring is below a threshold value;

increasing the first height to a second height; and forming the annular ring such that the annular ring has the second height;

wherein:

the threshold value is 10 mm.

109. The method of claim 107 wherein the point is the highest point on the roof in the image.

110. The method of claim 107 wherein the image is a cross-sectional view of the heart chamber taken along an apical long axis of the heart chamber.

111. The method of claim 110 wherein:

the side of the heart is a left side of the heart; and the cross-sectional view passes through a center of a mitral valve orifice and a left ventricular apex.

112. The method of claim 107 wherein:

the heart chamber is a left atrium; and the roof of the heart chamber is within 0.5-1.5 mm of a bifurcation of a pulmonary trunk and a right pulmonary artery.

113. The method of claim 107 wherein:

the heart chamber is a right atrium; and the roof of the heart chamber is a surface parallel to an interatrial septum and spaced vertically above a tricuspid annulus at a superior atrial wall.

114. The method of claim 107 further comprising forming the implant from a superelastic material such that an outer face of the implant is an atraumatic surface and the implant is collapsible for deployment into the heart chamber and thereafter expandable such that the implant:

is anchorable within the heart chamber by pressured contact with the heart chamber; and does not pierce heart tissue.

115. The method of claim 114 wherein the curved portion, when expanding in the heart chamber, undergoes movement in response to pressure from walls of the heart chamber, wherein the movement converges an implant axis with a central axis of the heart chamber.

116. The method of claim 115 wherein the central axis of the heart chamber:

extends through a highest anatomical point of the heart chamber; and is oblique relative to a vertical axis extending from a midpoint of the level to a top of the heart chamber vertically above the midpoint.

117. The method of claim 115 wherein the movement is absent a force applied by an instrument.

118. The method of claim 117 wherein the movement is driven by an expansion force of the curved portion and a shape of the heart chamber.

119. The method of claim 115 wherein the implant axis is a central axis of the implant.

120. The method of claim 115 wherein the implant axis extends along a central axis of the curved portion.

121. The method of claim 115 wherein the movement positions a top of the implant at a highest anatomical point of the heart chamber.

122. The method of claim 115 wherein the movement positions a hub of the implant at a highest anatomical point of the heart chamber.

123. The method of claim 122 wherein the movement does not occur when the implant axis is aligned with a central axis of the heart chamber.

124. The method of claim 115 further comprising forming an annular ring extending away from the curved portion, the annular ring being sized to be anchored in an annulus of the side of the heart, the annulus defining the upper annular surface, wherein:

the movement aligns an annular ring central axis with the central axis of the heart chamber.

125. The method of claim 124 wherein the curved portion maintains alignment of the annular ring central axis with the central axis of the heart chamber during a heart cycle.

126. The method of claim 125 wherein:

the heart chamber is an atrium and the side of the heart includes a ventricle; and the alignment of the annular ring central axis with the central axis of the heart chamber during systole provides blood flow impingement on a posterior side of the ventricle.

* * * * *